United States Patent
Nakamura et al.

(10) Patent No.: US 12,274,538 B2
(45) Date of Patent: Apr. 15, 2025

(54) MAGNETIC FIELD MEASURING APPARATUS, MAGNETIC FIELD MEASURING METHOD, AND RECORDING MEDIUM STORING MAGNETIC FIELD MEASURING PROGRAM

(71) Applicant: Asahi Kasei Microdevices Corporation, Tokyo (JP)

(72) Inventors: Takenobu Nakamura, Tokyo (JP); Shigeki Okatake, Tokyo (JP); Yoshitaka Moriyasu, Tokyo (JP); Makoto Kataoka, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 1096 days.

(21) Appl. No.: 17/176,201

(22) Filed: Feb. 16, 2021

(65) Prior Publication Data

US 2021/0161420 A1    Jun. 3, 2021

Related U.S. Application Data

(63) Continuation of application No. PCT/JP2019/032548, filed on Aug. 21, 2019.

(30) Foreign Application Priority Data

Aug. 22, 2018   (JP) ................ 2018-155832

(51) Int. Cl.
*A61B 5/05*    (2021.01)
*G01N 27/82*   (2006.01)
*G01N 33/20*   (2019.01)

(52) U.S. Cl.
CPC .............. *A61B 5/05* (2013.01); *G01N 27/82* (2013.01); *G01N 33/20* (2013.01);
(Continued)

(58) Field of Classification Search
CPC ........ G01N 27/82; G01N 33/20; G01R 33/02; G01R 33/09; G01R 35/00; H10N 50/10;
(Continued)

(56) References Cited

U.S. PATENT DOCUMENTS 5,642,045 A    6/1997 Keefe
5,764,061 A    6/1998 Asakawa
(Continued)

FOREIGN PATENT DOCUMENTS

DE    102011083961 A1    4/2013
EP    1795864 A1    6/2007
(Continued)

OTHER PUBLICATIONS

Koichiro Kobayashi et al. "Development of Biomagnetic Measurement System with 39ch SQUIDs Magnetometer for a Three Dimensional Magnetic Measurement" T.IEE Japan, vol. 118 Issue 11,1998, pp. 524-531.
(Continued)

*Primary Examiner* — Mark D Remaly

(57) ABSTRACT

A magnetic field measuring apparatus is provided including: a magnetic sensor array configured so that a plurality of magnetic sensor cells including a plurality of magnetic sensors each having a magnetoresistive element and magnetic flux concentrators arranged on both ends of the magnetoresistive element are three-dimensionally arranged and capable of detecting a magnetic field in three axial directions; a magnetic field acquiring section configured to acquire measurement data measured by the magnetic sensor array; and a signal space separating section configured to perform signal separation on a spatial distribution of a magnetic field indicated by the measurement data, based on
(Continued)

basis vectors calculated from orthonormal functions and a position and magnetic sensitivity of each magnetic sensor of the magnetic sensor array.

18 Claims, 18 Drawing Sheets

(52) U.S. Cl.
    CPC .............. *A61B 2560/0223* (2013.01); *A61B 2562/0223* (2013.01); *A61B 2562/046* (2013.01)

(58) Field of Classification Search
    CPC .... A61B 2560/0223; A61B 2562/0223; A61B 2562/046; A61B 5/05
    See application file for complete search history.

(56) References Cited

U.S. PATENT DOCUMENTS

| | | | |
|---|---|---|---|
| 5,990,679 | A | 11/1999 | Frommer |
| 6,376,933 | B1 | 4/2002 | Goetz |
| 6,841,994 | B1 | 1/2005 | Wiegert |
| 7,342,399 | B1 | 3/2008 | Wiegert |
| 7,603,251 | B1 | 10/2009 | Wiegert |
| 2001/0026222 | A1 | 10/2001 | Canady |
| 2003/0011767 | A1 | 1/2003 | Imura |
| 2004/0155644 | A1 | 8/2004 | Stauth |
| 2004/0207396 | A1 | 10/2004 | Xiao |
| 2004/0232912 | A1 | 11/2004 | Tsukamoto |
| 2004/0263162 | A1 | 12/2004 | Kandori |
| 2005/0030018 | A1 | 2/2005 | Shibahara |
| 2005/0212515 | A1 | 9/2005 | Watanabe |
| 2006/0031038 | A1 | 2/2006 | Simola |
| 2006/0055402 | A1 | 3/2006 | Seki |
| 2006/0066295 | A1 | 3/2006 | Tamura |
| 2007/0108962 | A1 | 5/2007 | Taulu |
| 2007/0108975 | A1 | 5/2007 | Desplats |
| 2008/0161714 | A1 | 7/2008 | Ahonen |
| 2008/0294386 | A1 | 11/2008 | Taulu |
| 2009/0069661 | A1 | 3/2009 | Taulu |
| 2009/0184709 | A1 | 7/2009 | Kajola |
| 2010/0277163 | A1 | 11/2010 | Nakamura |
| 2010/0327862 | A1 | 12/2010 | Nagasaka |
| 2011/0074406 | A1 | 3/2011 | Mather |
| 2013/0109954 | A1 | 5/2013 | Simola |
| 2013/0150702 | A1 | 6/2013 | Hokari |
| 2013/0165766 | A1 | 6/2013 | Nishikawa |
| 2013/0214774 | A1 | 8/2013 | Cesaretti |
| 2014/0111197 | A1 | 4/2014 | Lortie |
| 2014/0257104 | A1 | 9/2014 | Dunbar |
| 2014/0343882 | A1 | 11/2014 | Taulu |
| 2015/0070008 | A1 | 3/2015 | Motz |
| 2015/0145625 | A1 | 5/2015 | Fukasawa |
| 2015/0168176 | A1 | 6/2015 | Wu |
| 2015/0212166 | A1 | 7/2015 | Kandori |
| 2015/0253412 | A1 | 9/2015 | Jost |
| 2015/0331072 | A1 | 11/2015 | Ogawa |
| 2016/0037277 | A1 | 2/2016 | Matsumoto |
| 2016/0041006 | A1 | 2/2016 | Ausserlechner |
| 2016/0174867 | A1 | 6/2016 | Hatano |
| 2016/0360987 | A1 | 12/2016 | Miyasaka |
| 2017/0090003 | A1 | 3/2017 | Guo |
| 2017/0100051 | A1 | 4/2017 | Honkura |
| 2017/0212188 | A1 | 7/2017 | Kikitsu |
| 2017/0219661 | A1 | 8/2017 | Hata |
| 2017/0248665 | A1 | 8/2017 | Ludwig |
| 2017/0299662 | A1 | 10/2017 | Nagasaka |
| 2017/0299663 | A1 | 10/2017 | Nagasaka |
| 2018/0014738 | A1 | 1/2018 | Tanaka |
| 2018/0193728 | A1 | 7/2018 | Bashkirov |
| 2018/0242865 | A1 | 8/2018 | Yamagata |
| 2018/0284310 | A1 | 10/2018 | Jiro |
| 2018/0292468 | A1 | 10/2018 | Guo |
| 2018/0340987 | A1 | 11/2018 | Latham |
| 2019/0079141 | A1 | 3/2019 | Marauska |
| 2019/0125268 | A1 | 5/2019 | Taulu |
| 2019/0133478 | A1 | 5/2019 | Varcoe |
| 2019/0242956 | A1 | 8/2019 | Przytarski |
| 2019/0293735 | A1 | 9/2019 | Ushioda |
| 2019/0298202 | A1 | 10/2019 | Nakamura |
| 2020/0166343 | A1 | 5/2020 | Vissiere |
| 2020/0326399 | A1 | 10/2020 | Yoshida |
| 2021/0161420 | A1 | 6/2021 | Nakamura |
| 2021/0286023 | A1 | 9/2021 | Okatake |
| 2022/0065953 | A1 | 3/2022 | Tsuji |

FOREIGN PATENT DOCUMENTS

| | | |
|---|---|---|
| JP | H01196586 A | 8/1989 |
| JP | H03200083 A | 9/1991 |
| JP | 105232202 A | 9/1993 |
| JP | H09243725 A | 9/1997 |
| JP | 2000051169 A | 2/2000 |
| JP | 2000217798 A | 8/2000 |
| JP | 2000284032 A | 10/2000 |
| JP | 2001083224 A | 3/2001 |
| JP | 2001087237 A | 4/2001 |
| JP | 2001281311 A | 10/2001 |
| JP | 2002272695 A | 9/2002 |
| JP | 2003199723 A | 7/2003 |
| JP | 2004271303 A | 9/2004 |
| JP | 2005049179 A | 2/2005 |
| JP | 2005195376 A | 7/2005 |
| JP | 2005217341 A | 8/2005 |
| JP | 2006047080 A | 2/2006 |
| JP | 2007285865 A | 11/2007 |
| JP | 2008032562 A | 2/2008 |
| JP | 2008142154 A | 6/2008 |
| JP | 2011047910 A | 3/2011 |
| JP | 2011220977 A | 11/2011 |
| JP | 2012152514 A | 8/2012 |
| JP | 2012152515 A | 8/2012 |
| JP | 2013217690 A | 10/2013 |
| JP | 2014134388 A | 7/2014 |
| JP | 2014153054 A | 8/2014 |
| JP | 2014153309 A | 8/2014 |
| JP | 2015075465 A | 4/2015 |
| JP | 2016065829 A | 4/2016 |
| JP | 2016183944 A | 10/2016 |
| JP | 2017003312 A | 1/2017 |
| JP | 2017026312 A | 2/2017 |
| JP | 2017062122 A | 3/2017 |
| JP | 6153387 A | 6/2017 |
| JP | 2017133933 A | 8/2017 |
| JP | 2017166921 A | 9/2017 |
| JP | 2018004286 A | 1/2018 |
| JP | 2018004618 A | 1/2018 |
| JP | 2018054461 A | 4/2018 |
| JP | 2020148760 A | 9/2020 |
| WO | 03046587 A1 | 6/2003 |
| WO | 2005030051 A1 | 4/2005 |
| WO | 2017209273 A1 | 12/2017 |

OTHER PUBLICATIONS

International Search Report and (ISA/237) Written Opinion of the International Search Authority for International Patent Application No. PCT/JP2019/050826, mailed by the Japan Patent Office on Mar. 17, 2020.
Office Action issued for counterpart Japanese Application No. 2018-157607, issued by the Japanese Patent Office on Jan. 29, 2019 (drafted on Jan. 23, 2019).
Office Action issued for counterpart Japanese Application No. 2018-157607, issued by the Japanese Patent Office on Oct. 23, 2018 (drafted on Oct. 12, 2018).
Office Action issued for related U.S. Appl. No. 16/809,502, issued by the US Patent and Trademark Office on Apr. 26, 2022.
Hu Chao et al.,"A cubic 3-axis magnetic sensor array for wirelessly tracking magnet position and orientation." IEEE Sensors Journal 10.5 (2010): 903-913. (Year: 2010).

(56) References Cited

OTHER PUBLICATIONS

Three-Axis Magnetic Sensor H MC 1043 Datasheet (Year: 2012), Aug. 2012.
Office Action issued for counterpart U.S. Appl. No. 16/365,689, issued by the US Patent and Trademark Office on Mar. 7, 2022.
Office Action issued for counterpart U.S. Appl. No. 16/434,192, issued by the US Patent and Trademark Office on Mar. 25, 2021.
Office Action issued for counterpart U.S. Appl. No. 16/434,192, issued by the US Patent and Trademark Office on Apr. 13, 2022.
Office Action issued for counterpart U.S. Appl. No. 16/365,689, issued by the US Patent and Trademark Office on Sep. 29, 2022.
Office Action issued for counterpart U.S. Appl. No. 16/434,192, issued by the US Patent and Trademark Office on Dec. 29, 2021.
Office Action issued for counterpart U.S. Appl. No. 16/434,192, issued by the US Patent and Trademark Office on Sep. 27, 2022.
International Search Report and (ISA/237) Written Opinion of the International Search Authority for International Patent Application No. PCT/JP2019/032548, issued/mailed by the Japan Patent Office on Oct. 21, 2019.
Samu Taula et al., "Presentation of electromagnetic multichannel data: The signal space separation method", Journal of Applied Physics 97, 124905 (2005),pp. 124905-1-124905-10.
Kensuke Skihara, "Signal Space Separation Method for a Biomagnetic Sensor Array Arranged on a Flat Plane for Magnetocardiographic Applications: A Computer Simulation Study", Journal of Healthcare Engineering vol. 2018, Article ID 7689589, pp. 1-19, https://doi.org/10.1155/2018/7689589.
Samu Taulu et al., "Applications of the Signal Space Separation Method", IEEE Transactions on Signal Processing, vol. 53, No. 9, Sep. 2005,pp. 3359-3372.
Samu Taulu et al., "Spatiotemporal signal space separation method for rejecting nearby interference in MEG measurements", Institute of Physics Publishing, Physics in Medicine and Biology, UK, 2006, 51, 1759-1768.

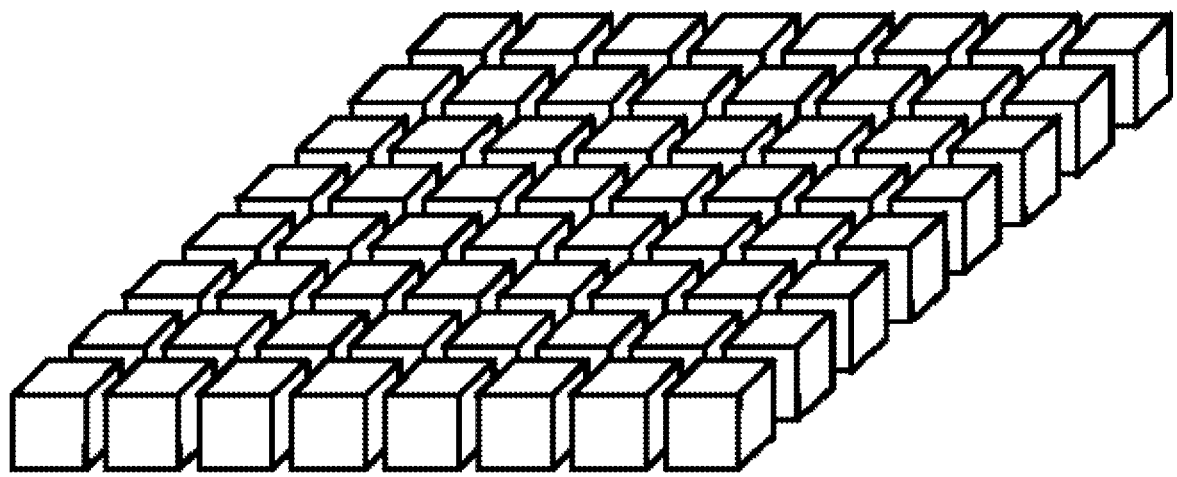
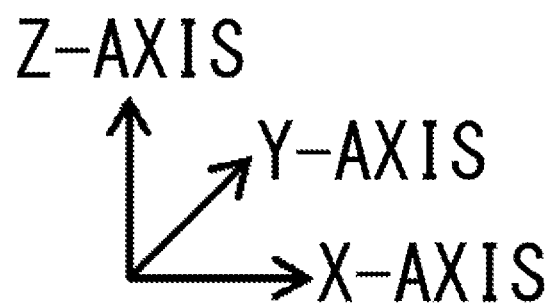
FIG. 12A

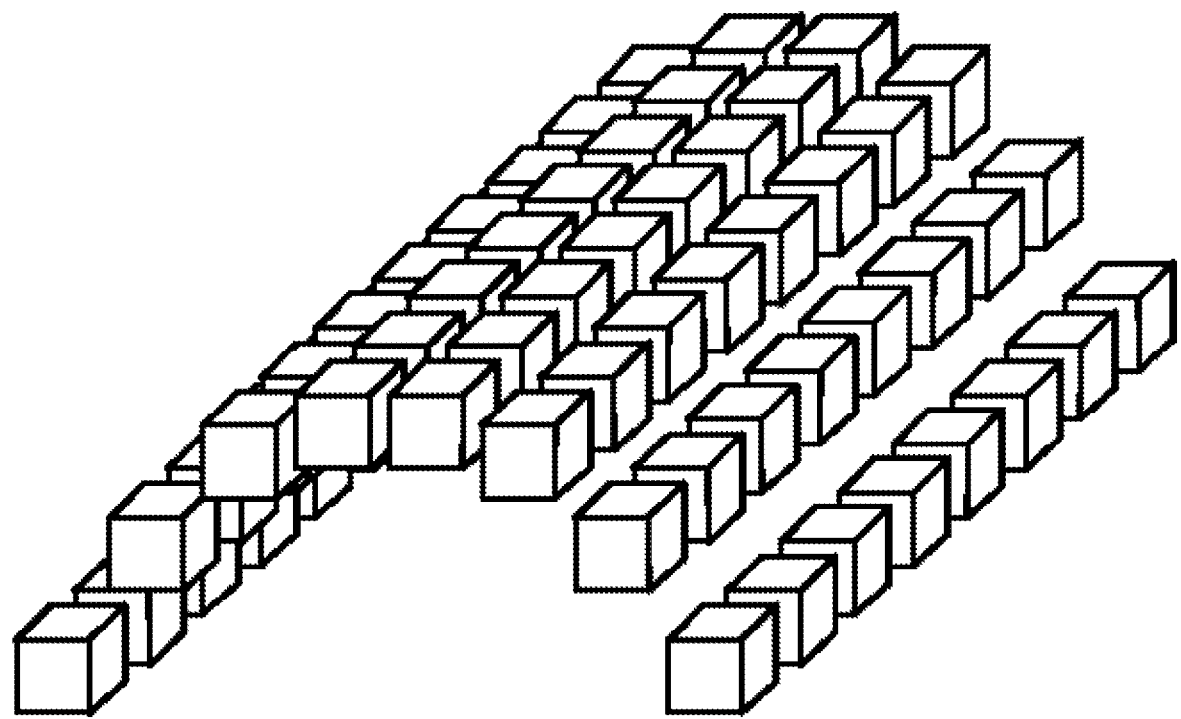
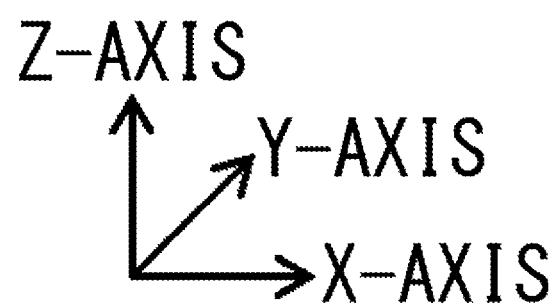
FIG. 12B

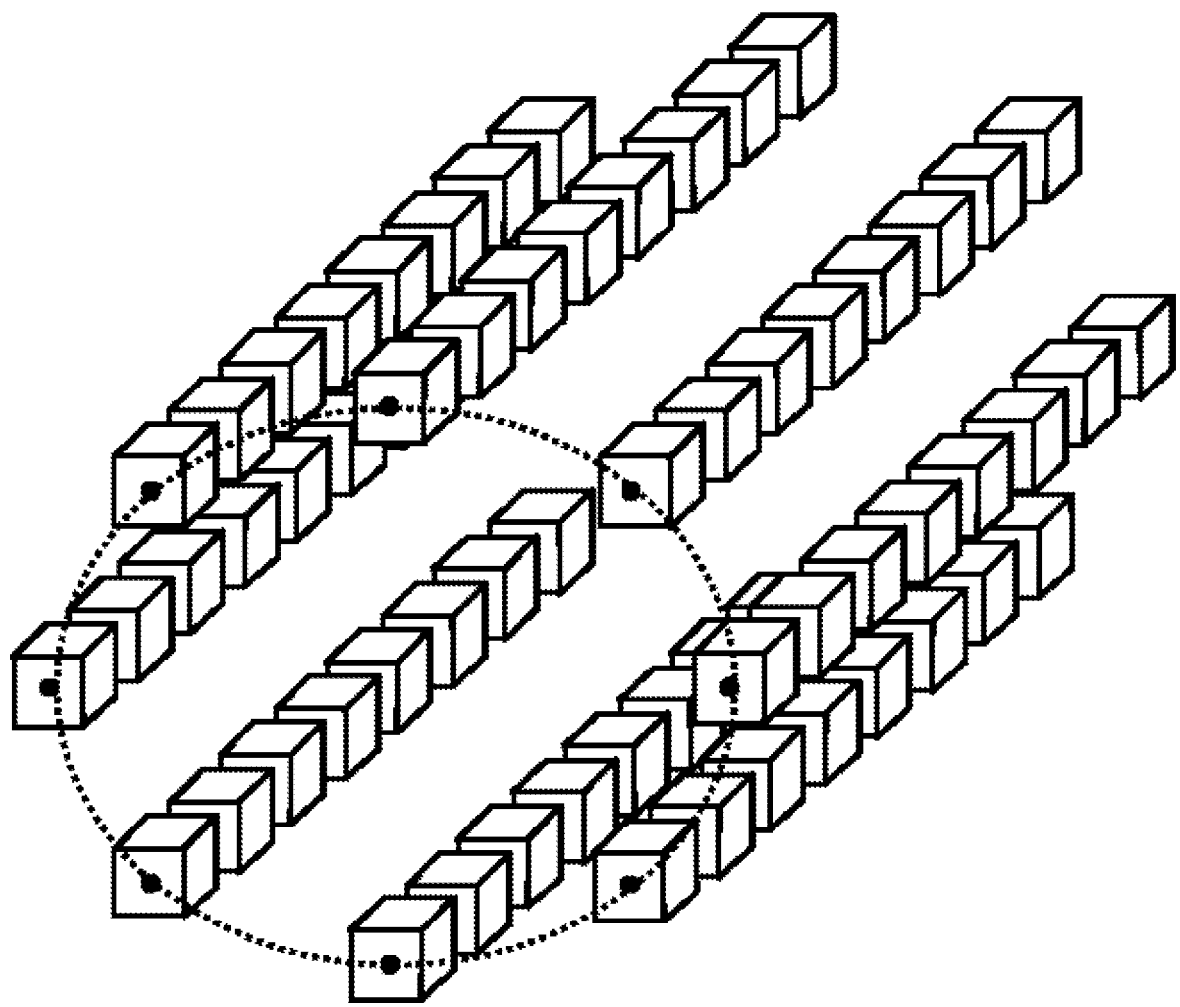
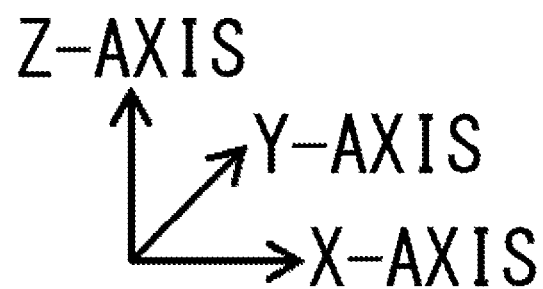
FIG. 12C

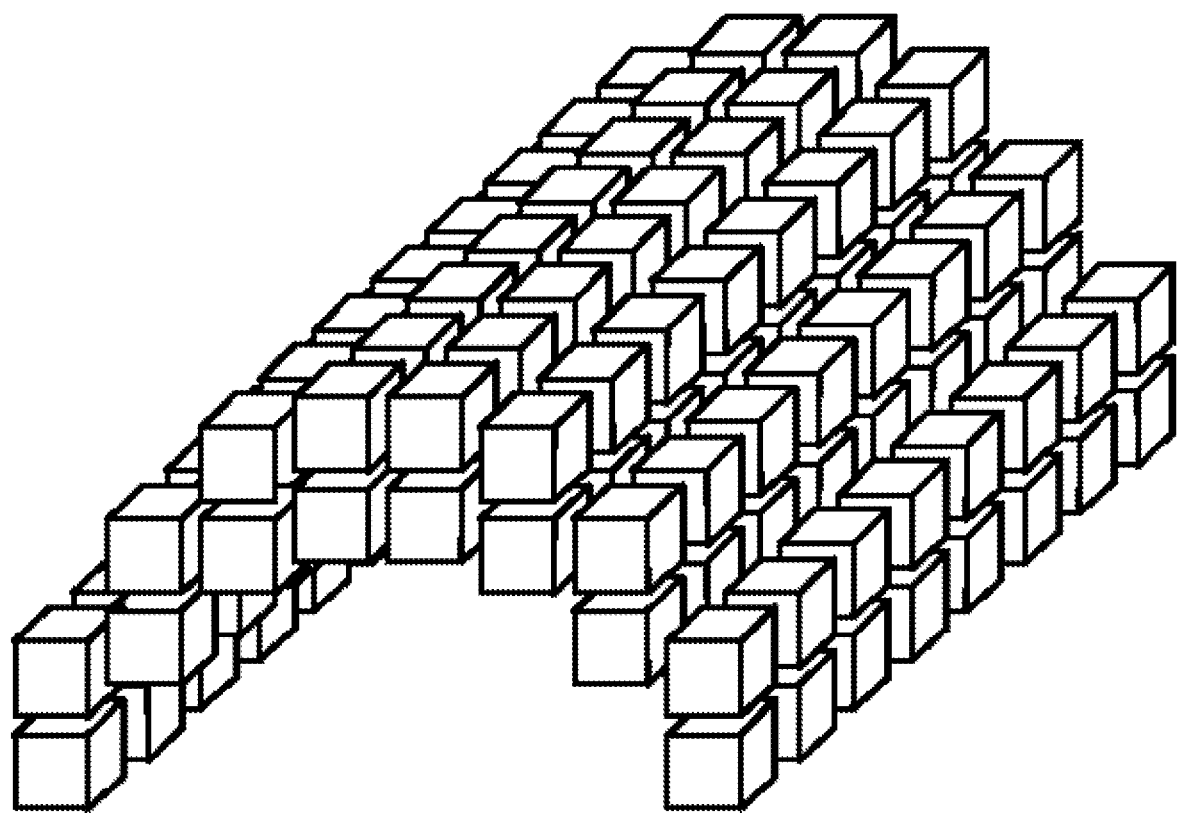
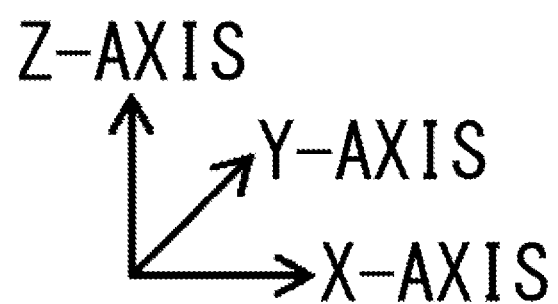
FIG. 12D

MAGNETIC FIELD MEASURING APPARATUS, MAGNETIC FIELD MEASURING METHOD, AND RECORDING MEDIUM STORING MAGNETIC FIELD MEASURING PROGRAM

The contents of the following Japanese patent application are incorporated herein by reference:
NO. 2018-155832 filed in JP on Aug. 22, 2018
NO. PCT/JP2019/032548 filed in WO on Aug. 21, 2019

BACKGROUND

1. Technical Field

The present invention relates to a magnetic field measuring apparatus, a magnetic field measuring method, and a recording medium storing a magnetic field measuring program.

2. Related Art

Conventionally, a magnetic field measuring apparatus that measures a magnetic field emitted from the head or the chest of a subject, using a sensor platform board having a plurality of Tunnel Magneto-Resistance (TMR) elements arranged in an array form has been known (see, for example, Patent Document 1). Patent Document 1: Japanese Patent Application Publication No. 2012-152514

The conventional magnetic field measuring apparatus, with a pair of magnetic detection elements stacked in a magnetic field detection direction, has measured a to-be-measured magnetic field with a disturbance magnetic field suppressed, based on the following mechanism. Specifically, the disturbance magnetic field results in the same magnitude between the measurement results of the pair of magnetic detection elements, whereas the to-be-measured magnetic field results in different magnitudes between the measurement results of the pair of magnetic detection elements. Nevertheless, for a more accurate inspection on a living subject, implementation of a magnetic field measuring apparatus capable of more accurately measuring a to-be-measured magnetic field has been desired.

SUMMARY

To solve the problem described above, a first aspect of the present invention provides a magnetic field measuring apparatus. The magnetic field measuring apparatus may include a magnetic sensor array configured so that a plurality of magnetic sensor cells including a plurality of magnetic sensors each having a magnetoresistive element are three-dimensionally arranged and capable of detecting a magnetic field in three axial directions. The magnetic field measuring apparatus may include a magnetic field acquiring section configured to acquire measurement data measured by the magnetic sensor array.

The magnetic field measuring apparatus may include a signal space separating section configured to perform signal separation on a spatial distribution of the magnetic field indicated by the measurement data, based on basis vectors calculated from orthonormal functions, a position and magnetic sensitivity of each magnetic sensor of the magnetic sensor array.

Each of the magnetic sensor cells may include a magnetic field generating section configured to generate a feedback magnetic field to reduce an input magnetic field detected by each of the magnetic sensors, and an output section configured to output an output signal corresponding to a feedback current that is to flow for the magnetic field generating section to generate the feedback magnetic field.

The signal space separating section may perform the signal separation to separate the spatial distribution of the magnetic field into a to-be-measured magnetic field and a disturbance magnetic field.

The signal space separating section may suppress the disturbance magnetic field to calculate the to-be-measured magnetic field.

The signal space separating section may perform the signal separation on the spatial distribution of the magnetic field, through series expansion of the basis vectors.

The signal space separating section may calculate coefficients of the basis vectors using a least-squares method.

The orthonormal functions may be expressed with spherical harmonics.

The magnetic sensors may each further include magnetic flux concentrators arranged on both one end and the other end of the magnetoresistive element.

A calibration calculating section configured to calibrate the measurement data acquired by the magnetic field acquiring section may be further provided.

The magnetic sensor array may be formed in two stages.

In the magnetic sensor array, the magnetic sensor cells may be three-dimensionally arranged to be positioned at grid points between two curved surfaces curved in one direction.

The curved surface shapes may be formed to be substantially parabolic.

A second aspect of the present invention provides a magnetic field measuring method with which a magnetic field measuring apparatus measures a magnetic field. The magnetic field measuring method may include acquiring, by the magnetic field measuring apparatus, measurement data measured by a magnetic sensor array configured so that a plurality of magnetic sensor cells including a plurality of magnetic sensors each having a magnetoresistive element are three-dimensionally arranged and capable of detecting a magnetic field in three axial directions. The magnetic field measuring method may include performing, by the magnetic field measuring apparatus, signal separation on a spatial distribution of the magnetic field indicated by the measurement data, based on basis vectors calculated from orthonormal functions and a position and magnetic sensitivity of each magnetic sensor of the magnetic sensor array. Each of the magnetic sensor cells may generate a feedback magnetic field to reduce an input magnetic field detected by each of the magnetic sensors and output an output signal corresponding to a feedback current that is to flow for generating the feedback magnetic field.

A third aspect of the present invention provides a recording medium storing a magnetic field measuring program. The magnetic field measuring program may be executed by a computer. The magnetic field measuring program may cause the computer to function as a magnetic field acquiring section configured to acquire measurement data measured by a magnetic sensor array configured so that a plurality of magnetic sensor cells including a plurality of magnetic sensors each having a magnetoresistive element are three-dimensionally arranged and capable of detecting a magnetic field in three axial directions. The magnetic field measuring program may cause the computer to function as a signal space separating section configured to perform signal separation on a spatial distribution of the magnetic field indicated by the measurement data, based on basis vectors calculated from orthonormal functions and a position and magnetic sensitivity of each magnetic sensor of the magnetic sensor array. Each of the magnetic sensor cells may generate a feedback magnetic field to reduce an input magnetic field detected by each of the magnetic sensors and output an output signal corresponding to a feedback current that is to flow for generating the feedback magnetic field.

The summary clause does not necessarily describe all necessary features of the embodiments of the present invention. The present invention may also be a sub-combination of the features described above.

BRIEF DESCRIPTION OF THE DRAWINGS

FIG. 12A illustrates a magnetic sensor arrays 210 having a first shape (a) used for simulating a disturbance attenuation ratio.

FIG. 12B illustrates a magnetic sensor arrays 210 having a second shape (b) used for simulating a disturbance attenuation ratio.

FIG. 12C illustrates a magnetic sensor arrays 210 having a third shape (c) used for simulating a disturbance attenuation ratio.

FIG. 12D illustrates a magnetic sensor arrays 210 having a fourth shape (2b) used for simulating a disturbance attenuation ratio.

DESCRIPTION OF EXEMPLARY EMBODIMENTS

Hereinafter, the present invention will be described through embodiments of the invention. However, the following embodiments do not limit the invention defined in the claims. Also, all combinations of features described in the embodiments are not necessarily essential to solutions of the invention.

Figure 1:
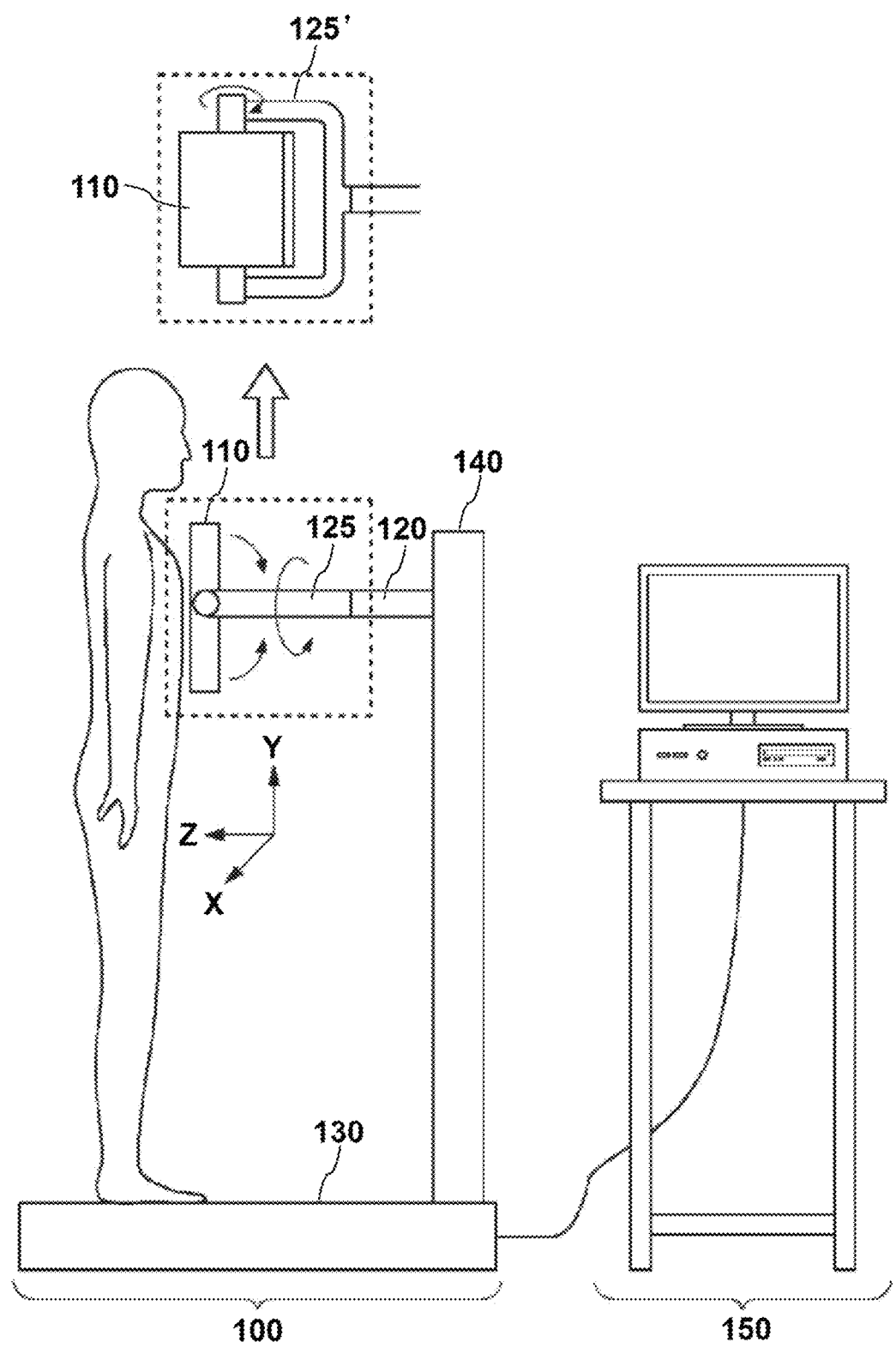
FIG. 1 illustrates a configuration of a magnetic field measuring apparatus 10 according to the present embodiment.

FIG. 1 illustrates a configuration of a magnetic field measuring apparatus 10 according to the present embodiment. The magnetic field measuring apparatus 10 measures a magnetic field using a magnetoresistive element. The magnetic field measuring apparatus 10 is one example of a magnetocardiographic measuring apparatus, and measures a magnetic field (referred to as a "cardiac magnetic field") generated by an electrical activity of a human heart. Alternatively, the magnetic field measuring apparatus 10 may be used for measuring the cardiac magnetic field of a living subject other than human, or may be used for measuring a biomagnetic field other than the cardiac magnetic field, such as a brain magnetic field. Furthermore, the magnetic field measuring apparatus 10 may be used for magnetic particle testing for detecting surface and subsurface flaws or the like of iron and steel materials and welded parts.

The magnetic field measuring apparatus 10 includes a main body 100 and an information processing section 150. The main body 100 is a component for sensing the cardiac magnetic field of a subject, and includes a magnetic sensor unit 110, a head 120, a driving section 125, a base portion 130, and a pole portion 140.

The magnetic sensor unit 110 is arranged at a position facing the heart in the chest of the subject during a magnetocardiographic measurement, and senses the cardiac magnetic field of the subject. The head 120 supports the magnetic sensor unit 110, and causes the magnetic sensor unit 110 to face the subject. The driving section 125 is provided between the magnetic sensor unit 110 and the head 120, and changes the orientation of the magnetic sensor unit 110 relative to the head 120 when performing calibration. The driving section 125 according to the present embodiment includes a first actuator that can cause the magnetic sensor unit 110 to rotate 360 degrees about a Z-axis in the drawing and a second actuator that causes the magnetic sensor unit 110 to rotate about an axis perpendicular to the Z-axis (an X-axis for the state in the drawing), and changes the azimuth angle and zenith angle of the magnetic sensor unit 110 using these actuators. As illustrated by the driving section 125 in the drawing, the driving section 125 is Y-shaped when viewed from the Y-axis direction in the drawing, and the second actuator can cause the magnetic sensor unit 110 to rotate 360 degrees about the X-axis in the drawing.

The base portion 130 is a base platform that supports other components, and is a platform the subject steps on during a magnetocardiographic measurement in the present embodiment. The pole portion 140 supports the head 120 at the height of the chest of the subject. The pole portion 140 may be capable of extending and contracting in an up-down direction in order to adjust the height of the magnetic sensor unit 110 to the height of the chest of the subject.

The information processing section 150 is a component for processing measurement data obtained by the main body 100 and outputting this data through printing, displaying, or the like. The information processing section 150 may be a computer such as a PC (personal computer), a tablet computer, a smartphone, a workstation, a server computer, or a general-purpose computer, or may be a computer system in which a plurality of computers are connected. Alternatively, the information processing section 150 may be a dedicated computer designed for information processing for magnetocardiographic measurement, or may be dedicated hardware implemented by a dedicated line.

Figure 2:
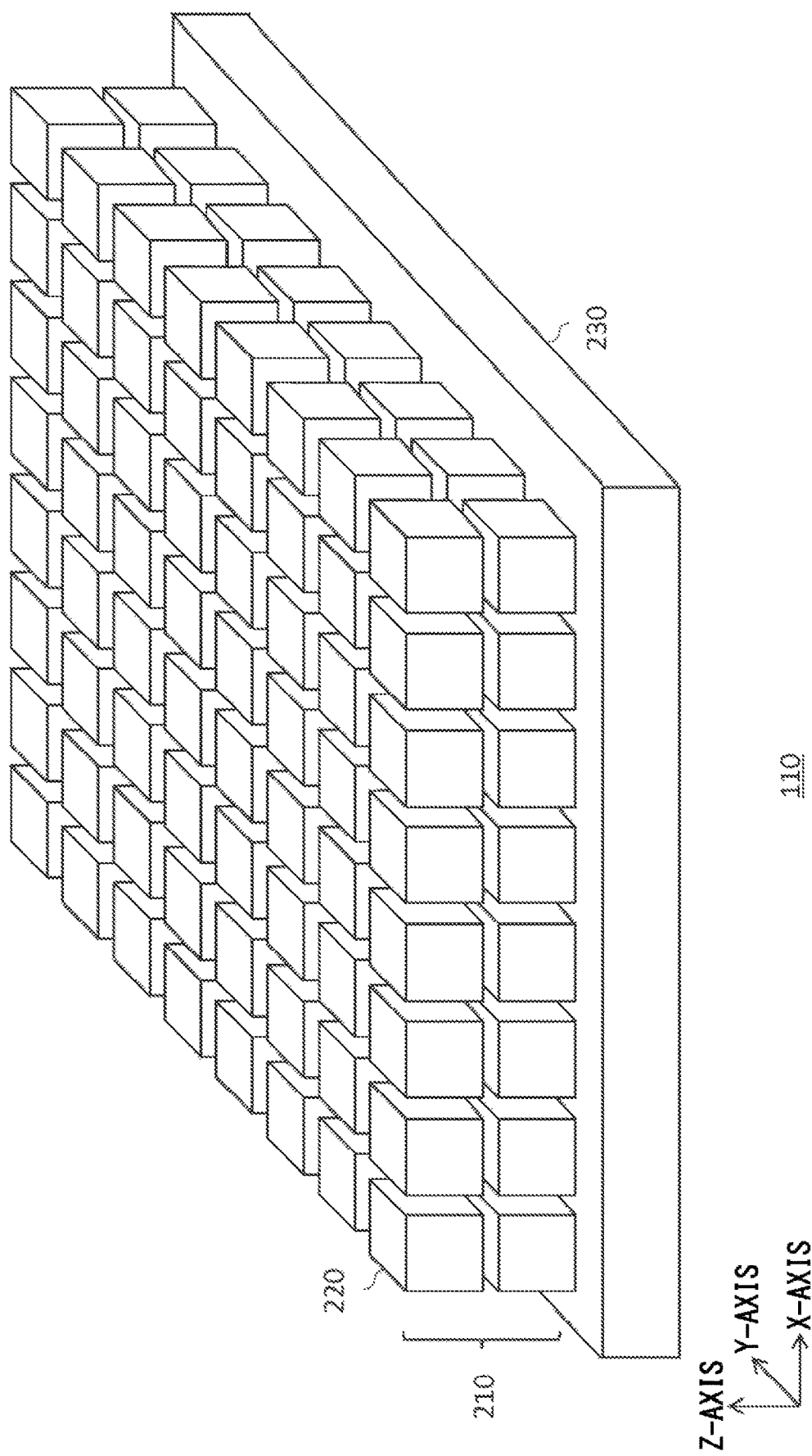
FIG. 2 illustrates a configuration of a magnetic sensor unit 110 according to the present embodiment.

FIG. 2 illustrates a configuration of the magnetic sensor unit 110 according to the present embodiment. The magnetic sensor unit 110 includes a magnetic sensor array 210 and a sensor data gathering section 230. The magnetic sensor array 210 is configured so that a plurality of magnetic sensor cells 220, including a plurality of magnetic sensors each having a magnetoresistive element and a magnetic flux concentrator(s) that is arranged on at least one of both one end and the other end of the magnetoresistive element or on both ends of the magnetoresistive element, are three-dimensionally arranged and capable of detecting a magnetic field in three axial directions. Note that, preferably, the magnetic flux concentrators are arranged on both ends of the magnetoresistive element, so that sampling of a spatial distribution of the magnetic field described later can be implemented with a higher accuracy. In the present drawing, the plurality of magnetic sensor cells 220 in the magnetic sensor array 210 are arranged in a planar shape, in each of the X direction, the Y direction, and the Z direction (for example, a total of 128 magnetic sensor cells 220 with 8 cells arranged in the X direction, 8 cells arranged in the Y direction, and 2 cells arranged in the Z direction).

The sensor data gathering section 230 is electrically connected to the plurality of magnetic sensor cells 220 included in the magnetic sensor array 210 (not illustrated in the drawings), gathers sensor data (detection signals) from the plurality of magnetic sensor cells 220, and supplies this sensor data to the information processing section 150.

Figure 3:
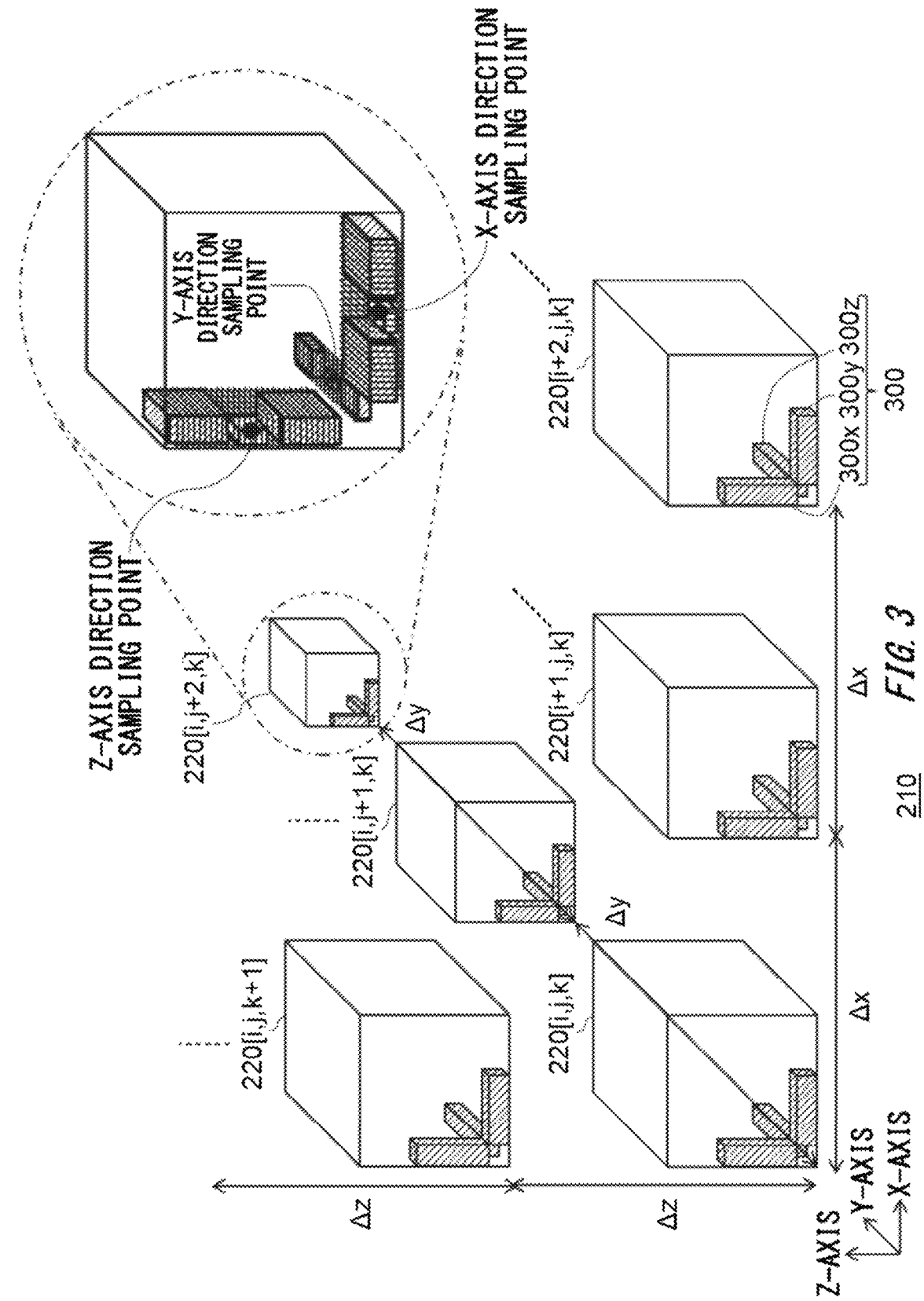
FIG. 3 illustrates a configuration and arrangement of a magnetic sensor cells 220 in a magnetic sensor array 210 according to the present embodiment.

FIG. 3 illustrates a configuration and arrangement of the magnetic sensor cells 220 in the magnetic sensor array 210 according to the present embodiment. Each magnetic sensor cell 220 includes a plurality of sensor sections 300x to z (hereinafter, collectively referred to as a "sensor section 300") each including a magnetoresistive element. In the present embodiment, the sensor sections 300x are arranged along the X-axis direction, and are capable of detecting a magnetic field in the X-axis direction. The sensor sections 300y are arranged along the Y-axis direction and are capable of detecting a magnetic field in the Y-axis direction. The sensor sections 300z are arranged along the Z-axis direction and are capable of detecting a magnetic field in the Z-axis direction. As illustrated in an enlarged view shown in a dash-dot line part of the present drawing, in the present embodiment, the sensor sections 300 each have the magnetic flux concentrators arranged on both ends of the magnetoresistive element. Thus, each sensor section 300 uses the magnetoresistive element arranged in a narrow position sandwiched between the magnetic flux concentrators to perform the sampling of the spatial distribution of the magnetic field, so that spatial sampling points can be clarified in each axis direction. The details of the configuration of each sensor section 300 are described later.

The plurality of magnetic sensor cells 220 are arranged at regular intervals $\Delta x$, $\Delta y$, and $\Delta z$, respectively along the X-axis direction, the Y-axis direction, and the Z-axis direction. The position of each magnetic sensor cell 220 in the magnetic sensor array 210 is expressed by a set [i, j, k] of a position i in the X direction, a position j in the Y direction, and a position k in the Z direction. Here, i is an integer satisfying $0<=i<=Nx-1$ (Nx represents the number of magnetic sensor cells 220 arranged in the X direction), j is an integer satisfying $0<=j<=Ny-1$ (Ny represents the number of magnetic sensor cells 220 arranged in the Y direction), and k is an integer satisfying $0<=k<=Nz-1$ (Nz represents the number of magnetic sensor cells 220 arranged in the Z direction).

In the present drawing, the three axial directions of the magnetic field detected by the sensor sections 300x, 300y, and 300z are the same direction as those of the three dimensions in which the magnetic sensor cells 220 are arranged. Therefore, it is easy to understand each component of the distribution of the measured magnetic field. The sensor sections 300x, 300y, and 300z are arranged in each of the magnetic sensor cells 220 so as not to overlap with each other in any of the three-dimensional directions in which the magnetic sensor cells 220 are arranged. Furthermore, in the present drawing, the sensor sections 300x, 300y, and 300z are arranged to extend along the respective three axial directions, to each have one end provided on the side of a gap provided between the plurality of sensor sections 300 and the other end provided away from the gap. As one example, the present drawing illustrates an example where an air space (gap) is formed at the lower left corner portion in front view of the magnetic sensor cell 220, and the sensor sections 300x, 300y, and 300z are arranged to respectively extend in the X-axis, the Y-axis, and the Z-axis directions, so that one end of each sensor section is in contact with the air space and the other end is away from the air space. In the present drawing, the sensor sections 300x, 300y, and 300z are arranged along three sides orthogonal to each other from one corner portion of the magnetic sensor cell 220 having a cubic shape, with an air space provided at the one corner portion. Preferably, coils or magnetic materials of the sensor sections 300x, 300y, and 300z described later are arranged without overlapping with each other. With this arrangement, the measurement points can be clarified, so that each component of the measured magnetic field is recognized more easily. The cross-axis sensitivities of the sensor sections 300x, 300y, and 300z may be regarded as being equal to each other. The cross-axis sensitivities result from mutual interference between the coils or the magnetic materials of the sensor sections 300x, 300y, and 300z. However, the three axial directions in which the magnetic field is detected may instead be different from the three dimensional directions in which the magnetic sensor cells 220 are arranged. When these directions are different from each other, no restriction on the arrangement of the sensor sections 300 in the magnetic sensor cells 220 and the arrangement direction of the magnetic sensor cells 220 can increase the degree of freedom in design of the magnetic sensor array 210.

Figure 4:
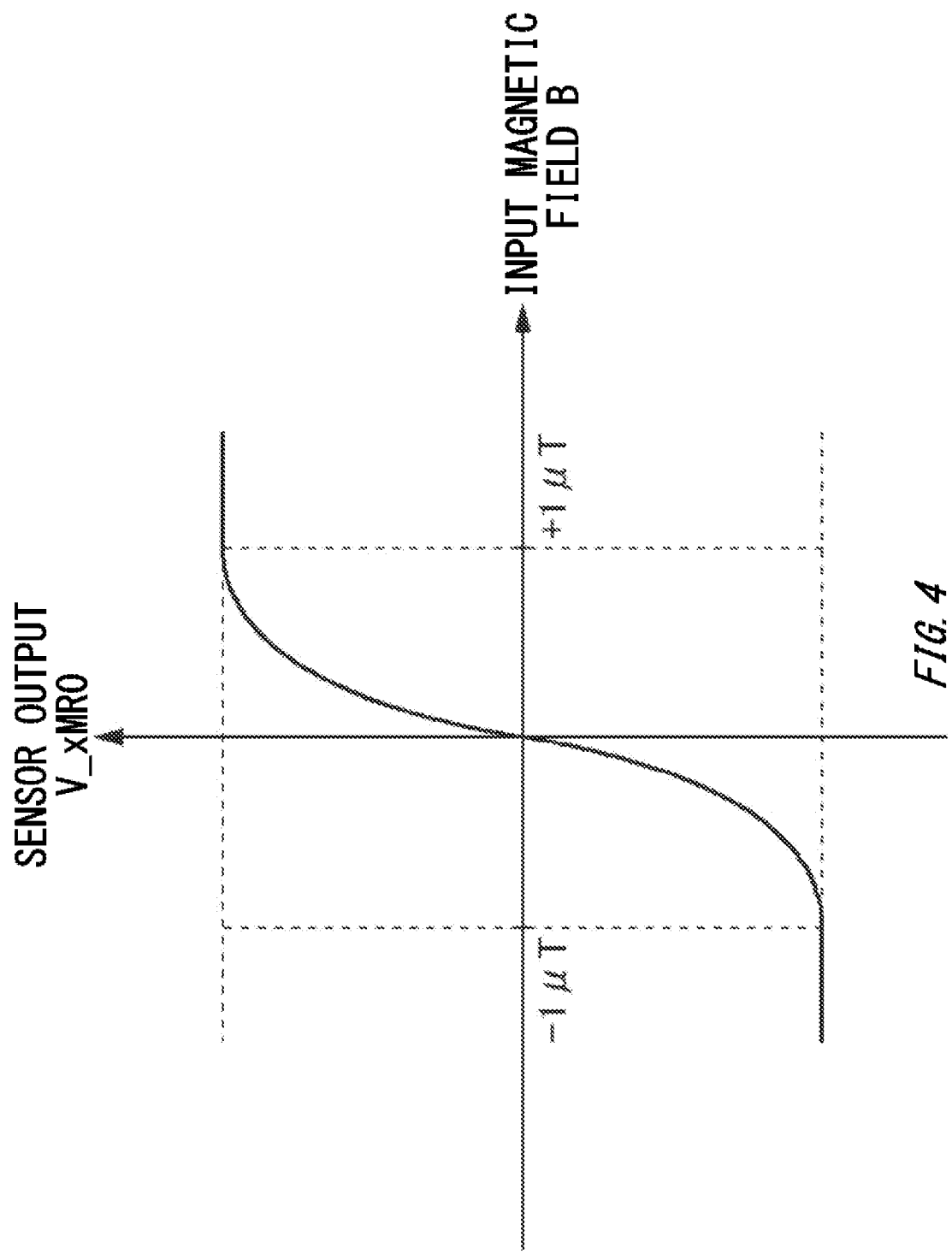
FIG. 4 illustrates an example of an input/output characteristic of a magnetic sensor having a magnetoresistive element according to the present embodiment.

FIG. 4 illustrates an example of an input/output characteristic of the magnetic sensor having the magnetoresistive element according to the present embodiment. In the present drawing, the horizontal axis indicates a magnitude B of an input magnetic field that is input to the magnetic sensor, and the vertical axis indicates a magnitude V_xMR0 of a detection signal of the magnetic sensor. For example, the magnetic sensor includes a Giant Magneto-Resistance (GMR) element, a Tunnel Magneto-Resistance (TMR) element, or the like, and detects the magnitude of the magnetic field in one predetermined axial direction.

Such a magnetic sensor has high magnetic sensitivity, which is the slope of the detection signal V_xMR0 relative to the input magnetic field B, and can detect a very small magnetic field of approximately 10 pT. At the same time, however, the detection signal V_xMR0 becomes saturated when the absolute value of an input magnetic field B is approximately 1 μT, for example, and the magnetic sensor has a narrow range in which the linearity of the input/output characteristic is good. Thus, adding a closed loop that generates a feedback magnetic field to such a magnetic sensor can improve the linearity of the magnetic sensor. The following describes such a magnetic sensor.

Figure 5:
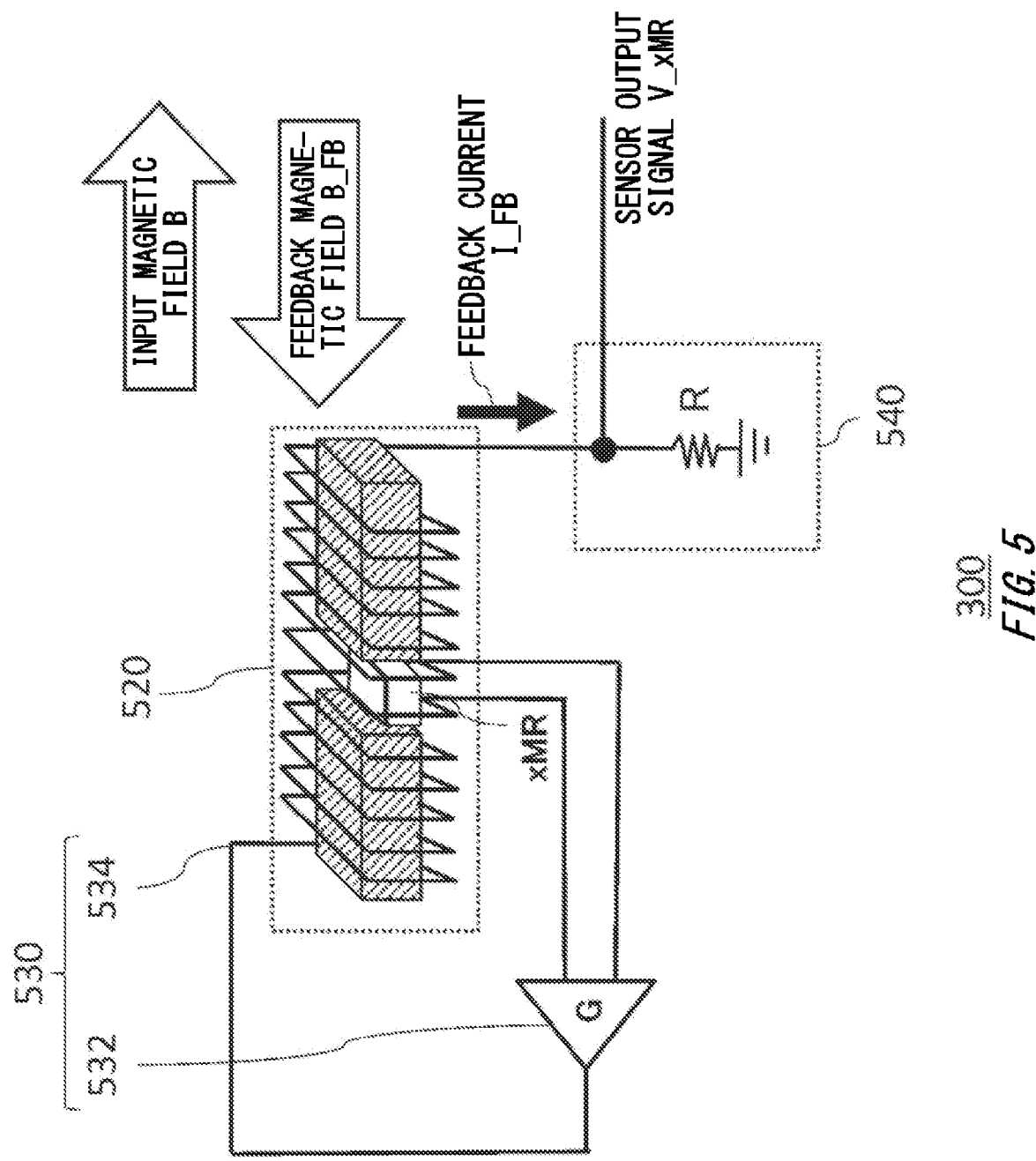
FIG. 5 illustrates an example of a configuration of a sensor section 300 according to the present embodiment.

FIG. 5 illustrates an example of a configuration of a sensor section 300 according to the present embodiment. The sensor sections 300 are provided in each of the plurality of magnetic sensor cells 220, and include a magnetic sensor 520, a magnetic field generating section 530, and an output section 540. Note that, a part of the sensor section 300, for example, an amplifier circuit 532 and the output section 540, may be provided on the side of the sensor data gathering section 230 rather than on the side of the magnetic sensor cells 220.

The magnetic sensor 520 includes a magnetoresistive element such as a GMR element or a TMR element, similar to the magnetic sensor described in FIG. 4. The magnetic sensor 520 further includes magnetic flux concentrators arranged on both ends of the magnetoresistive element. When a positive direction of the magnetosensitive axis is defined as a +X direction, the magnetoresistive element of the magnetic sensor 520 may be formed so that a resistance value increases in response to an input of a magnetic field in a +X direction and the resistance value decreases in response to an input of a magnetic field in a −X direction. Thus, observing a change in the resistance value of the magnetoresistive element of the magnetic sensor 520 can detect the magnitude of the magnetic field B input to the magnetic sensor 520. For example, when the magnetic sensitivity of the magnetic sensor 520 is S, the detection result of the magnetic sensor 520 for the input magnetic field B can be calculated as S×B. As one example, the magnetic sensor 520 is connected to a power source or the like, and outputs a voltage drop corresponding to the change of the resistance value, as a detection result of the input magnetic field. The details of the configuration of the magnetic sensor 520 are described later.

The magnetic field generating section 530 provides a feedback magnetic field for reducing the input magnetic field detected by the magnetic sensor 520, to the magnetic sensor 520. For example, the magnetic field generating section 530 operates to cause the generation of a feedback magnetic field B_FB having an orientation that is the opposite of the orientation of the magnetic field B input to the magnetic sensor 520 and an absolute value that is substantially the same as that of the input magnetic field, to cancel out the input magnetic field. The magnetic field generating section 530 includes the amplifier circuit 532 and a coil 534.

The amplifier circuit 532 outputs, as a feedback current I_FB, a current corresponding to the detection result of the input magnetic field of the magnetic sensor 520. When the magnetoresistive element of the magnetic sensor 520 is configured by a bridge circuit including at least one magnetoresistive element, an output of the bridge circuit is connected to each of a pair of input terminals of the amplifier circuit 532. The amplifier circuit 532 outputs a current corresponding to the output of the bridge circuit, as the feedback current I_FB. The amplifier circuit 532 includes a transconductance amplifier, for example, and outputs the feedback current I_FB corresponding to the output voltage of the magnetic sensor 520. For example, when a voltage-current conversion coefficient of the amplifier circuit 532 is G, the feedback current I_FB can be calculated as G×S×B.

The coil 534 generates a feedback magnetic field B_FB corresponding to the feedback current I_FB. The coil 534 is wound to surround the magnetoresistive element and the magnetic flux concentrators arranged on both ends of the magnetoresistive element of the magnetic sensor 520. The coil 534 preferably generates the feedback magnetic field B_FB to be uniform across the entire magnetic sensor 520. For example, when a coil coefficient of the coil 534 is β, the feedback magnetic field B_FB can be calculated as β×I_FB. Here, the feedback magnetic field B_FB is generated with an orientation that cancels out the input magnetic field B, and therefore the magnetic field input to the magnetic sensor 520 is reduced to B−B_FB. Accordingly, the feedback current I_FB is illustrated by the expression below.

$$I\_FB = G \times S \times (B - \beta \times I\_FB) \qquad \text{[Expression 1]}$$

When Expression 1 is solved for the feedback current I_FB, it is possible to calculate the value of the feedback current I_FB in a steady state of the sensor section 300. The expression below is calculated from Expression 1, assuming that the magnetic sensitivity S of the magnetic sensor 520 and the voltage-current conversion coefficient G of the amplifier circuit 532 are sufficiently large.

$$I\_FB = \frac{G \times S \times B}{1 + G \times S \times \beta} \cong \frac{B}{\beta} \qquad \text{[Expression 2]}$$

The output section 540 outputs an output signal V_xMR corresponding to the feedback current I_FB that is to flow in order for the magnetic field generating section 530 to generate the feedback magnetic field B_FB. For example, the output section 540 includes a resistance element with a resistance value R, and outputs a voltage drop, caused by the feedback current I_FB flowing through this resistance element, as the output signal V_xMR. In this case, the output signal V_xMR is calculated from Expression 2 as illustrated in the expression below.

$$V\_xMR = R \times I\_FB = \frac{R \times B}{\beta} \qquad \text{[Expression 3]}$$

As described above, the sensor section 300 generates the feedback magnetic field that reduces the magnetic field input thereto from the outside, and therefore the magnetic field substantially input to the magnetic sensor 520 is reduced. Thus, the sensor section 300 can prevent the detection signal V_xMR from being saturated, for example by using the magnetoresistive element having the characteristic illustrated in FIG. 4 as the magnetic sensor 520, even when the absolute value of the input magnetic field B exceeds 1 μT. The following describes the input/output characteristic of such a sensor section 300.

Figure 6:
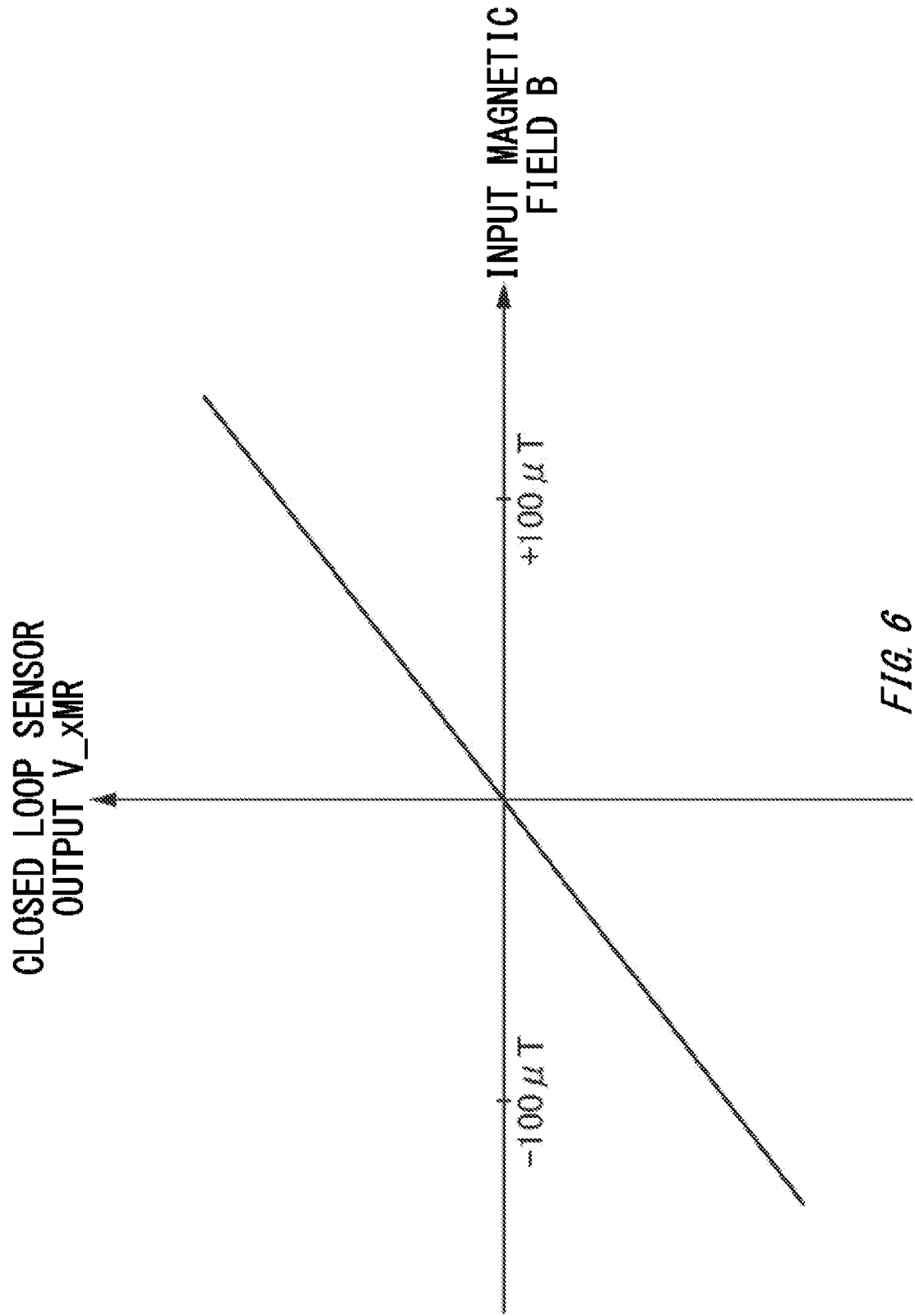
FIG. 6 illustrates an example of an input/output characteristic of the sensor section 300 according to the present embodiment.

FIG. 6 illustrates one example of an input/output characteristic of the sensor section 300 according to the present embodiment. In the present drawing, the horizontal axis indicates the magnitude B of the input magnetic field input to the sensor section 300, and the vertical axis indicates the magnitude V_xMR of the detection signal of the sensor section 300. The sensor section 300 has high magnetic sensitivity and can detect a very small magnetic field of approximately 10 pT. The sensor section 300 can also maintain good linearity of the detection signal V_xMR even when the absolute value of the input magnetic field B exceeds 100 µT, for example.

In other words, the sensor section 300 according to the present embodiment is configured such that the detection result for the input magnetic field B has linearity in a predetermined range of the input magnetic field B where the absolute value of the input magnetic field B is less than or equal to several hundred µT for example. Using such a sensor section 300 can detect a weak magnetic signal, for example, a cardiac magnetic field signal in a simple manner.

Figure 7:
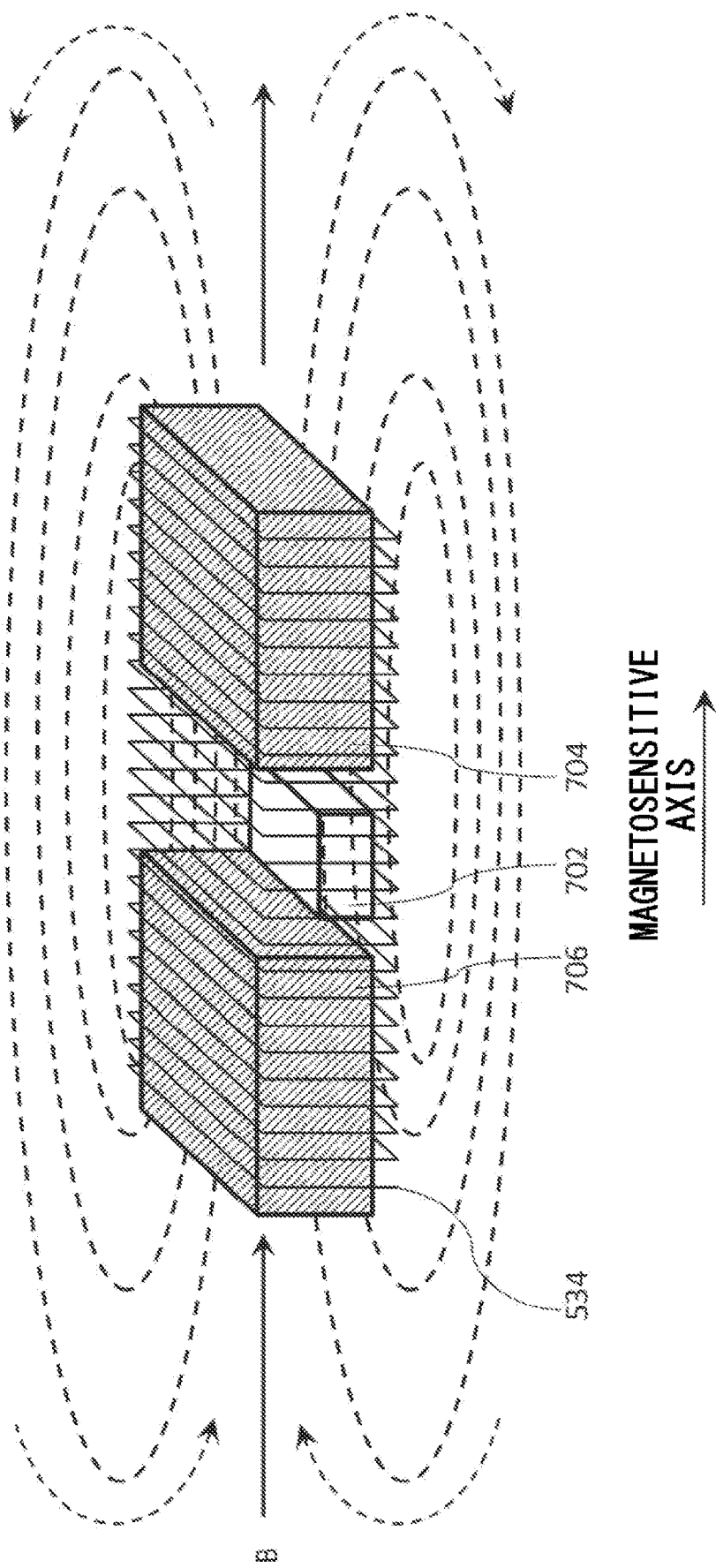
FIG. 7 illustrates an example of a configuration of a magnetic sensor 520 according to the present embodiment.

FIG. 7 illustrates an example of a configuration of a magnetic sensor 520 according to the present embodiment. As one example, the magnetic sensor 520 according to the present embodiment includes a magnetoresistive element 702 and magnetic flux concentrators 704 and 706 respectively arranged on one end and the other end of the magnetoresistive element 702. The magnetic flux concentrators 704 and 706 are arranged to sandwich the magnetoresistive element 702. That is, the magnetic flux concentrators are arranged on both ends of the magnetoresistive element 702. In FIG. 7, the magnetic flux concentrator 704 arranged on the right end of the magnetoresistive element 702 along the magnetosensitive axis in front view is a magnetic flux concentrator provided on the positive side of the magnetosensitive axis, and the magnetic flux concentrator 706 arranged on the left end of the magnetoresistive element 702 is a magnetic flux concentrator provided on the negative side of the magnetosensitive axis. Inputting a magnetic field, from the negative side toward the positive side of the magnetosensitive axis, to the magnetic flux concentrators 704 and 706 may increase or decrease the resistance of the magnetoresistive element 702. Note that, the magnetosensitive axis may extend along a magnetization direction fixed by a magnetization fixing layer forming the magnetoresistive element 702. The magnetic flux concentrators 704 and 706 are formed by a soft magnetic material such as iron, for example. Arranging the magnetic flux concentrators 704 and 706 formed by a soft magnetic material respectively on one end and the other end of the magnetoresistive element 702 can increase lines of magnetic force passing through the magnetoresistive element 702, thereby increasing the sensitivity of the magnetic sensor 520.

Although the present drawing illustrates an example where one end and the other end of the magnetoresistive element 702 are both provided with the magnetic flux concentrators, only either one of one end or the other end of the magnetoresistive element 702 may be provided with a magnetic flux concentrator. Still, both one end and the other end of the magnetoresistive element 702 are preferably provided with the magnetic flux concentrators, for the sake of higher sensitivity of the magnetic sensor 520. Furthermore, providing both one end and the other end of the magnetoresistive element 702 with the magnetic flux concentrators clarifies the magnetosensitive portion, because the position of the magnetoresistive element 702 arranged at a narrow position sandwiched by the two magnetic flux concentrators 704 and 706 is to be the magnetosensitive portion (spatial sampling point), so that affinity with a signal space separation technique described later can be enhanced more. Using, in each sensor section 300, the magnetic sensor 520 with the magnetic flux concentrators 704 and 706 arranged on both ends of the magnetoresistive element 702 enables the magnetic field measuring apparatus 10 according to the present embodiment to sample the spatial distribution of the magnetic field at an extremely narrow (equal to or smaller than 100 µm, for example) position, which is sandwiched on both ends by the magnetic flux concentrators in each axial direction, as illustrated in FIG. 3. Thus, a higher sampling accuracy (positional accuracy) can be achieved compared with a case where the spatial distribution of the magnetic field is sampled using a SQUID coil (up to 2 cm) for measuring a biomagnetic field.

Figure 8:
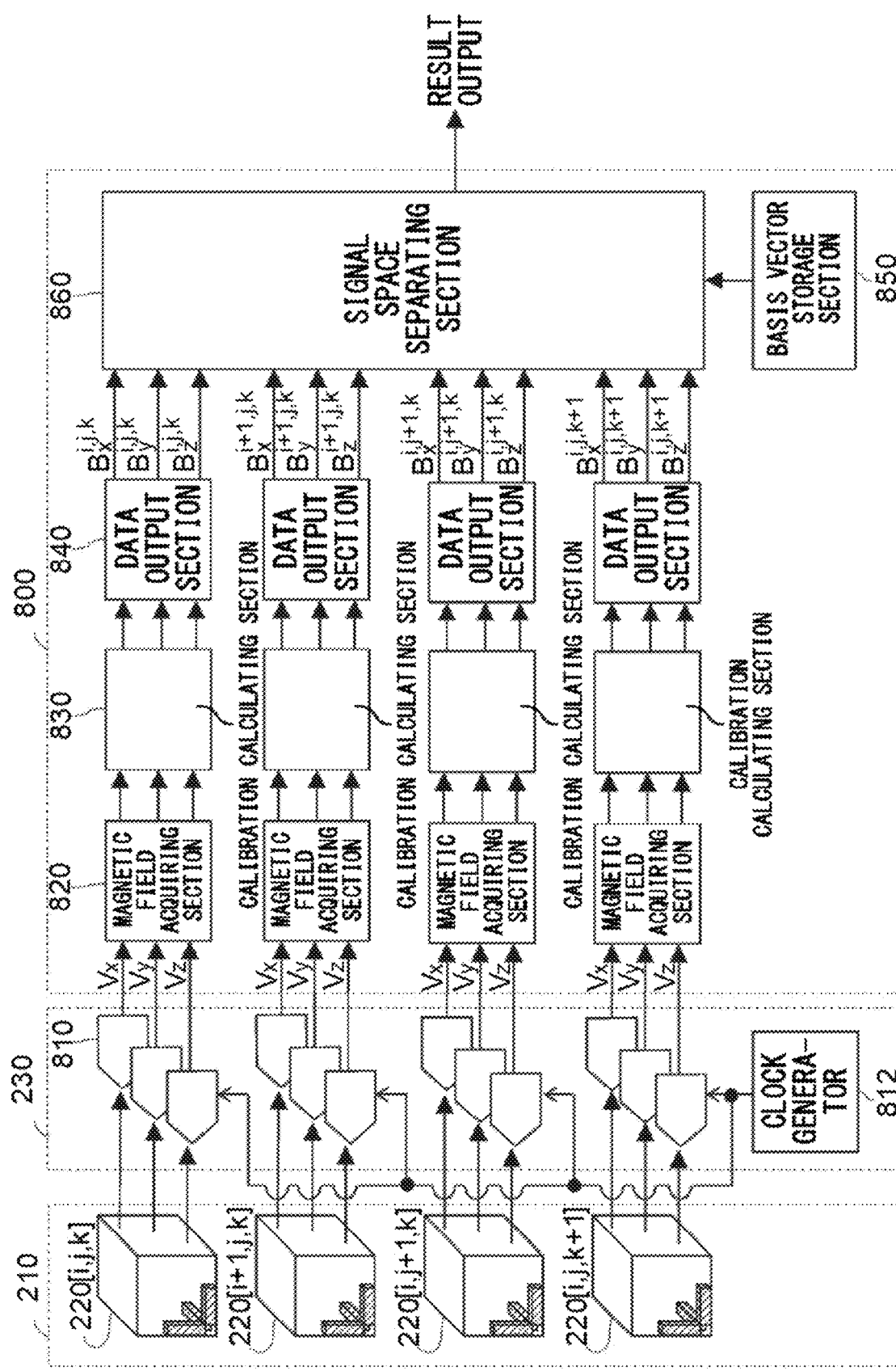
FIG. 8 illustrates a configuration of the magnetic sensor array 210, a sensor data gathering section 230, and a sensor data processing section 800 according to the present embodiment.

FIG. 8 illustrates a configuration of the magnetic sensor array 210, the sensor data gathering section 230, and a sensor data processing section 800 according to the present embodiment.

The magnetic sensor array 210 includes a plurality of the magnetic sensor cells 220. Each of magnetic sensor cells 220 includes the plurality of sensor sections 300$x$ to $z$ as described above. In the present drawing, among the plurality of magnetic sensor cells 220 included in the magnetic sensor array 210 in each dimensional direction, the portions relating to the positions [i, j, k], [i+1, j, k], [i, j+1, k], and [i, j, k+1] are illustrated.

The sensor data gathering section 230 includes a plurality of AD converters 810 and a clock generator 812. The AD converters 810 are each provided for a corresponding one of the sensor sections 300$x$ to $z$ of the magnetic sensor cells 220, and each convert an analog detection signal (sensor output signal V_xMR illustrated in FIG. 6) output from the corresponding sensor section 300 into digital measurement data (Vx, Vy, Vz). These Vx, Vy, and Vz are measurement values (representing digital voltage values, for example) obtained by digital conversion on the detection signals from the sensor sections 300$x$, 300$y$, and 300$z$.

The clock generator 812 generates a sampling clock and supplies a common sampling clock to each of the plurality of AD converters 810. Each of the plurality of AD converters 810 performs AD conversion according to the common sampling clock supplied from the clock generator 812. Thus, the AD converters 810 all operate in synchronization to perform AD conversion on the respective outputs from the three-axis sensor sections 300$x$ to $z$ provided at different positions. This enables the AD converters 810 to concurrently sample the detection results from the three-axis sensor sections 300$x$ to $z$ provided in different spaces.

The sensor data processing section 800 includes a plurality of magnetic field acquiring sections 820, a plurality of calibration calculating sections 830, and a plurality of data output sections 840 that are provided for each of the magnetic sensor cells 220, as well as a basis vector storage section 850 and a signal space separating section 860.

The magnetic field acquiring sections 820 are each connected to the three AD converters 810 connected to the corresponding one of the magnetic sensor cells 220, and acquire measurement data measured by each of the sensor sections 300$x$ to $z$ in the plurality of magnetic sensor cells 220 forming the magnetic sensor array 210. Specifically, the magnetic field acquiring section 820 may be configured using a flip-flop or the like that latches and acquires, at a predetermined timing T, the digital measurement data (Vx, Vy, Vz) digitally converted by the AD converter 810.

The calibration calculating section 830 is connected to the magnetic field acquiring section 820, and calibrates the measurement data acquired by the magnetic field acquiring section 820, by using a calibration parameter. An overview of the calibration for the measurement data performed by the calibration calculating section 830 is as follows. A magnetic field input to the magnetic sensor cell 220 at the position [i, j, k] is defined as B(Bx, By, Bz), and a detection result obtained by the three-axis magnetic sensor using the sensor sections 300$x$, 300$y$, and 300$z$ is defined as V(Vx, Vy, Vz). In this case, the detection result V obtained by the three-axis magnetic sensor can be expressed as in the expression below, where matrix S represents the magnetic sensor characteristics of the three-axis magnetic sensor.

$$S\begin{pmatrix} Bx \\ By \\ Bz \end{pmatrix} + \begin{pmatrix} Vos,x \\ Vos,y \\ Vos,z \end{pmatrix} = \begin{pmatrix} Sxx & Sxy & Sxz \\ Syx & Syy & Syz \\ Szx & Szy & Szz \end{pmatrix} \begin{pmatrix} Bx \\ By \\ Bz \end{pmatrix} + \begin{pmatrix} Vos,x \\ Vos,y \\ Vos,z \end{pmatrix} \quad \text{[Expression 4]}$$

In the expression, Sxx, Syy, and Szz represent sensitivities (main axis sensitivities) in the main axis direction of the respective sensor sections 300x, 300y, and 300z, and Sxy, Sxz, Syx, Syz, Szx, and Szy represent sensitivities (cross-axis sensitivities) in other axis directions. Furthermore, Vos,x, Vos,y, and Vos,z represent offsets of the respective sensor sections 300x, 300y, and 300z. Here, the main axis directions are directions in which the measurement by the sensor sections 300x, 300y, and 300z is mainly performed, whereas the other axis directions are directions in which the measurement by these magnetic sensor sections is not mainly performed. In the magnetic field measurement, the main axis direction is a direction in which the sensitivity of the magnetic sensor becomes the highest for a magnetic field that is input (input axis direction, sensitivity axis direction). The other axis directions are defined as axes orthogonal to the main axis direction. For example, when the sensor section 300x performs the measurement in the X-axis direction, the main axis direction is the X-axis, and the other axis directions are the Y-axis direction and the Z-axis direction. The magnetic sensor 520 ideally has the main axis sensitivity only, but may have cross-axis sensitivities due to process factors or the like. The magnetic sensor 520 also has the cross-axis sensitivities caused by the mutual interference described above. Note that a column vector expressed by three components including the main axis sensitivity and the cross-axis sensitivities of the sensor section 300 is referred to as a sensitivity vector. For example, a sensitivity vector nx of the sensor section 300x is expressed by three components (Sxx, Sxy, Sxz). In this case, the output from the sensor section 300x is an inner product between an input magnetic field to the sensor and the sensitivity vector nx. Similarly, a sensitivity vector ny of the sensor section 300y is expressed by three components (Syx, Syy, Syz), and a sensitivity vector nz of the sensor section 300z is expressed by three components (Szx, Szy, Szz).

A detection result of each of the sensor sections 300 has linearity for an input magnetic field to be detected within a range of the input magnetic field. Thus, each element of the matrix S becomes a substantially constant coefficient independent of the magnitude of the input magnetic field B. Even when the sensor section 300 has cross-axis sensitivities, each element of the matrix S becomes a substantially constant coefficient independent of the magnitude of the input magnetic field B, as long as the detection result of the sensor section 300 has linearity.

Thus, the calibration calculating section 830 can convert the measurement data V(Vx, Vy, Vz) into the magnetic field measurement data B (Bx, By, Bz) indicating the original input magnetic field by using an inverse matrix S-1 of the matrix S and the offset (Vos,x, Vos,y, Vos,z), as in the expression below. In other words, the calibration calculating section 830 calibrates the digital measurement data V from the magnetic field acquiring section 820 by using the main axis sensitivity, cross-axis sensitivities, and offset. This causes the calibration calculating section 830 to correct the offset, the sensitivity in the main axis direction, and the sensitivities in the other axis directions. This conversion can be also true even when the sensor sections 300x to z have the magnetic flux concentrators described above. This is because the magnetic sensor cell 220 is configured as a three-axis magnetic sensor using the sensor sections 300x to z, and because conversion using linear algebra can be performed. Note that providing a high-pass filter or the like in a section from the output of the sensor section 300 to the calibration calculating section 830 may omit the calibration for the offset, if the measurement data V is an AC component. Thus, the calibration calculating section 830 may calibrate the digital measurement data V from the magnetic field acquiring section 820 using at least one of the main axis sensitivity, cross-axis sensitivities, and offset. These calibration parameters may be calculated by measuring known DC or AC magnetic fields in advance. The calibration calculating section 830 in the present embodiment only needs to be capable of calibrating the output from each magnetic sensor cell 220 to components expressed by a coordinate system formed by three independent vectors, and does not necessarily need to correct the outputs to three-axis components expressed by a coordinate system (what is known as the Cartesian coordinate system) with three vectors orthogonal to each other. Thus, when all the magnetic sensor cells 220 measure the same magnetic field, the respective calibration calculating sections 830 corresponding to the respective magnetic sensor cells 220 may calibrate the digital measurement data V from the corresponding magnetic field acquiring section 820 to the same magnetic field measurement data B expressed by independent three-axis components.

$$\begin{pmatrix} Bx \\ By \\ Bz \end{pmatrix} = S^{-1} \left\{ \begin{pmatrix} Vx \\ Vy \\ Vz \end{pmatrix} - \begin{pmatrix} Vos,x \\ Vos,y \\ Vos,z \end{pmatrix} \right\} \quad \text{[Expression 5]}$$

The calibration calculating section 830 uses environment magnetic field measurement data to calculate the inverse matrix S-1 of the matrix S and the offset (Vos,x, Vos,y, Vos,z), converts the magnetic field measurement data acquired by the magnetic field acquiring section 820 into the magnetic field measurement data B using these calibration parameters, and supplies the magnetic field measurement data B to the data output section 840.

As each sensor section 300 has linearity as described above, the calibration calculating sections 830 can convert the measurement data into the magnetic field measurement data B using the substantially constant coefficients. Thus, the substantially constant coefficients used by the calibration calculating sections 830 can be defined as a set of calibration parameters using the environment magnetic field data.

The data output section 840 supplies the magnetic field measurement data B, calibrated by the calibration calculating section 830, to the signal space separating section 860.

The basis vector storage section 850 prestores basis vectors required for the signal space separating section 860 to perform signal separation on the magnetic field measurement data B, and supplies the basis vectors to the signal space separating section 860.

The signal space separating section 860 performs the signal separation on the spatial distribution of the magnetic field indicated by the magnetic field measurement data B supplied from the data output section 840, that is, the magnetic field measurement data B as a result of calibrating the digital measurement data V, using, as the basis vectors, signal vectors output from each of magnetic sensors 520 when the magnetic sensor array 210 detects a magnetic field having a spatial distribution of orthonormal functions. In this process, the signal space separating section 860 acquires the basis vectors required for the signal separation from the basis vector storage section 850. Then, the signal space separating section 860 uses the basis vectors acquired from the basis vector storage section 850 to perform the signal separation to separate the spatial distribution of the magnetic field indicated by the magnetic field measurement data B into a to-be-measured magnetic field (signal source spatial signal) and a disturbance magnetic field (disturbance spatial signal), to suppress the disturbance magnetic field and calculate the to-be-measured magnetic field, outputting the to-be-measured magnetic field.

Figure 9:
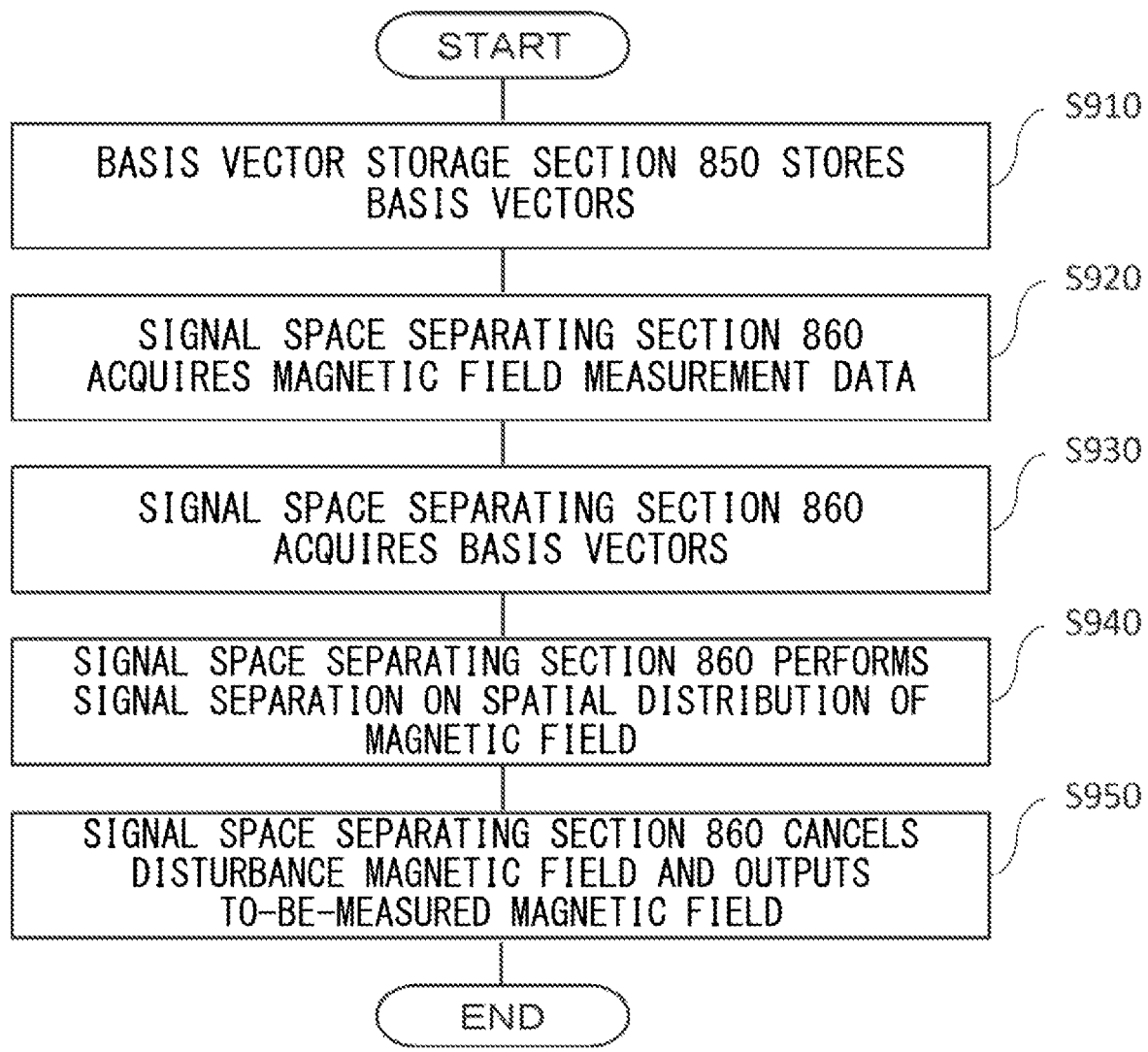
FIG. 9 illustrates a flow of signal separation performed by the magnetic field measuring apparatus 10 according to the present embodiment on a spatial distribution of a magnetic field.

FIG. 9 illustrates a flow of signal separation performed by the magnetic field measuring apparatus 10 according to the present embodiment on a spatial distribution of a magnetic field. In step 910, the basis vector storage section 850 stores the basis vectors. As one example, before the measurement of the to-be-measured magnetic field, the basis vector storage section 850 stores, as the basis vectors, signal vectors output from each of the magnetic sensors 520 when the magnetic sensor array 210 detects a magnetic field having a spatial distribution of spherical harmonics. Thus, the basis vectors may be calculated from the position and the sensitivity vector of each magnetic sensor of the magnetic sensor array 210, and may be stored in the basis vector storage section 850 in advance. Specifically, the basis vector storage section 850 stores, as the basis vectors, magnetic field signal vectors obtained by spatially sampling the spherical harmonics when a predetermined point in a space is designated as the coordinate origin. In other words, the basis vector storage section 850 calculates in advance magnetic field signal vectors expressing a magnetic field of a space with two subspaces (a signal source space and a disturbance space) through series expansion of the spherical harmonics, based on the position and the sensitivity vector of each magnetic sensor, and stores the resultant vectors as the basis vectors. Here, the spherical harmonics are functions obtained by restricting, to a unit sphere, the homogeneous polynomial that is a solution to an n-dimensional Laplace equation, and has orthonormality on the sphere. In one example illustrated in the present drawing, step 910 in which the basis vector storage section 850 stores the basis vectors is defined as the first step in the flow of signal separation on the spatial distribution of the magnetic field performed by the magnetic field measuring apparatus 10. Alternatively, the basis vector storage section 850 may prestore the basis vectors, before starting the flow of signal separation on the spatial distribution of the magnetic field performed by the magnetic field measuring apparatus 10. Furthermore, the basis vector storage section 850 may store, as the basis vectors, signal vectors predetermined from a simulation result or the like.

Next, in step 920, the signal space separating section 860 acquires the magnetic field measurement data B measured by the magnetic sensor array 210 and calibrated by the calibration calculating section 830, from the data output section 840.

In step 930, the signal space separating section 860 acquires the signal vectors stored as the basis vectors in the basis vector storage section 850 in step 910, from the basis vector storage section 850. In this flow, either one of step 920 or step 930 may be performed before the other.

In step 940, the signal space separating section 860 performs series expansion of the spatial distribution of the magnetic field indicated by the magnetic field measurement data B acquired in step 920, using the signal vectors acquired in step 930 as the basis vectors. The signal space separating section 860 performs the signal separation to separate the spatial distribution of the magnetic field into a to-be-measured magnetic field (signal source spatial signal) and a disturbance magnetic field (disturbance spatial signal), based on the vectors obtained by the series expansion. Note that the orthonormal functions may be spherical harmonics. The signal space separating section 860 calculates series expansion coefficients of the basis vectors by least-squares method, when the signal separation is performed.

In step 950, the signal space separating section 860 calculates and outputs only the to-be-measured magnetic field with the disturbance magnetic field suppressed based on a result of the signal separation in step 940, and the processing is terminated. This will be described in detail below.

With a potential V(r) satisfying a Laplace equation $\Delta V(r) = 0$, a static magnetic field B(r) is obtained as a spatial gradient of the potential V(r) as in the expression below. In the expression, r represents a position vector representing the position with respect to the coordinate origin, $\Delta$ represents a Laplacian, $\mu$ represents permeability, and $\nabla$ represents a vector differential operator.

$$B(r) = -\mu \nabla V(r) \quad \text{[Expression 6]}$$

Generally, a solution to the Laplace equation is in a form of series expansion using spherical harmonics $Y_{l,m}(\theta,\varphi)$ which are functions of an orthonormal function system, and thus the potential V(r) can be expressed as in the expression below. In the expression, |r| represents an absolute value (the distance from the coordinate origin) of the position vector r, $\theta$ and $\varphi$ represent two declinations of spherical coordinate, l represents an azimuthal quantum number, m represents a magnetic quantum number, $\alpha$ and $\beta$ represent multipole moments, and Lin and Lout are the numbers of series respectively in closer and farther spaces in the magnetic sensor array 210 as viewed from the subject. The azimuthal quantum number l is a positive integer, and the magnetic quantum number m is an integer in a range from −l to +l. In other words, when l is 1, for example, m is −1, 0, and 1, and when l is 2, for example, m is −2, −1, 0, 1, and 2. Since there is no case of a single magnetic pole in the magnetic field, the azimuthal quantum number l starts from 1 instead of 0 in Expression 7. The first term in Expression 7 is a term inverse proportional to a distance from the coordinate origin, and represents a potential in the closer space in the magnetic sensor array 210 as viewed from the subject. The second term in Expression 7 is a term proportional to a distance from the coordinate origin, and represents a potential in the closer space in the magnetic sensor array 210 as viewed from the subject.

$$V(r) = \sum_{l=1}^{Lin} \sum_{m=-l}^{l} \alpha_{l,m}\left(\frac{1}{|r|^{l+1}} Y_{l,m}(\theta,\phi)\right) + \sum_{l=1}^{Lout} \sum_{m=-l}^{l} \beta_{l,m}(|r|^l Y_{l,m}(\theta,\phi)) \quad \text{[Expression 7]}$$

Therefore, according to Expression 6 and Expression 7, the static magnetic field B(r) can be expressed by the expression below. Here, the first term in Expression 8 represents the cardiac magnetic field (to-be-measured magnetic field) generated by an electrical activity of the heart which is the magnetic field source in the closer space in the magnetic sensor array 210 as viewed from the subject. The second term in Expression 8 represents the disturbance magnetic field generated by the magnetic field source in the farther space in the magnetic sensor array 210 as viewed from the subject.

$$B(r) = -\mu \sum_{l=1}^{Lin} \sum_{m=-l}^{l} \alpha_{l,m} \nabla\left(\frac{1}{|r|^{l+1}} Y_{l,m}(\theta, \phi)\right) - \mu \sum_{l=1}^{Lout} \sum_{m=-l}^{l} \beta_{l,m} \nabla(|r|^l Y_{l,m}(\theta, \phi))$$

[Expression 8]

When the solution to the Laplace equation is expressed in a form of series expansion using the spherical harmonics, the general solution of such will be infinite series, but what needs to be obtained is a sufficient signal-to-noise ratio (SNR, which is a ratio of the to-be-measured magnetic field signal to the disturbance magnetic field and sensor noise) for measuring a biomagnetic field, which is regarded as being actually expressible with a series of about 10 terms. As the series for signal space separation in magnetoencephalogram, approximately Lin=8 and Lout=3 are generally used. Accordingly, also in the present embodiment, Lin and Lout may be values approximate to these. However, the Lin and Lout values are not limited to this, and may be any numerical values that are sufficient for sufficiently suppressing the disturbance magnetic field and calculating the to-be-measured magnetic field.

Here, al,m and bl,m are defined as in the expression below for all N sensors used in the magnetic sensor array 210. In the expression, n1, n2, . . . nN represent sensitivity vectors of the respective sensor sections. These al,m and bl,m are vectors with the number of dimensions obtained by multiplying the number of magnetic sensor cells 220 by three (because there are sensor sections 300x, y, and z). Thus, the number of dimensions of the vector corresponds to the number of all sensors. As one example, the vectors (al,m, bl,m) are calculated using data as a result of the calibration calculating section 830 correcting the output of each of the magnetic sensor cells 220. The values of al,m and bl,m, obtained by calculation thus including correction on sensitivities of the sensor section 300x, y, and z in the main axis direction and in the other axis directions (the corrected sensitivity vector), are stored in the basis vector storage section 850. The magnetic field measuring apparatus 10 according to the present embodiment in which the basis vector storage section 850 stores the values of al,m and bl,m, obtained by calculation including correction on the magnetic sensitivity (main axis sensitivity, cross-axis sensitivities) can correct the magnetic sensitivity of each magnetic sensor cell 220 (main axis sensitivity, cross-axis sensitivities) through the correction by the calibration calculating section 830 on the data acquired by the magnetic field acquiring section 820 during the operation. As another example, when the basis vector storage section 850 stores default values of al,m and bl,m (from uncorrected sensitivity vector) without correction on the magnetic sensitivity (main axis sensitivity, cross-axis sensitivities), the calibration calculating section 830 converts the output from each magnetic sensor cell 220 into data with the magnetic sensitivity corrected to match the default sensitivity vector of each sensor section as in Expression 5, the data is output to the data output section 840, and then the operation by the signal space separating section 860 is implemented.

$$a_{l,m} = -\mu \begin{bmatrix} \nabla\left(\frac{1}{r_1^{l+1}} Y_{l,m}(\theta_1, \phi_1)\right) \cdot n_1 \\ \nabla\left(\frac{1}{r_2^{l+1}} Y_{l,m}(\theta_2, \phi_2)\right) \cdot n_2 \\ \vdots \\ \nabla\left(\frac{1}{r_N^{l+1}} Y_{l,m}(\theta_N, \phi_N)\right) \cdot n_N \end{bmatrix}$$

$$b_{l,m} = -\mu \begin{bmatrix} \nabla(r_1^l Y_{l,m}(\theta_1, \phi_1)) \cdot n_1 \\ \nabla(r_2^l Y_{l,m}(\theta_2, \phi_2)) \cdot n_2 \\ \vdots \\ \nabla(r_N^l Y_{l,m}(\theta_N, \phi_N)) \cdot n_N \end{bmatrix}$$

[Expression 9]

With al,m and bl,m thus defined, a sensor output vector Φ output from each magnetic sensor cell 220 at a certain time point can be expressed as in the expression below.

$$\Phi = \sum_{l=1}^{Lin} \sum_{m=-l}^{l} \alpha_{l,m} a_{l,m} + \sum_{l=1}^{Lout} \sum_{m=-l}^{l} \beta_{l,m} b_{l,m}$$

[Expression 10]

Furthermore, Sin, Sout, Xin, and Xout are each defined in the following manner. Specifically, Sin is defined as a vector with a total of Lin×(Lin+2) columns in which vectors [a] that are respectively obtained with integers m=−1 to 1 with each of 1=1 to 1=Lin, and are arranged in columns in order. Furthermore, Sout is defined as a vector with a total of Lout×(Lout+2) columns in which vectors [b] that are respectively obtained with integers m=−1 to 1 with each of 1=1 to 1=Lout, and are arranged in columns in order. Furthermore, Xin is defined as a vector with a total of Lin×(Lin+2) columns as a result of transposing a vector in which multipole moments $\alpha_{l,m}$ that are respectively obtained with integers m=−1 to 1 with each of 1=1 to 1=Lin, and are arranged in columns in order. Furthermore, Xout is defined as a vector with a total of Lout×(Lout+2) columns as a result of transposing a vector in which multipole moments $\beta_{l,m}$ that are respectively obtained with integers m=−1 to 1 with each of 1=1 to 1=Lin, and are arranged in columns in order.

$Sin = [a_{1,-1} \ a_{1,0} \ a_{1,+1} \ \ldots \ a_{Lin,Lin}]$ $Sout = [b_{1,-1} \ b_{1,0} \ b_{1,+1} \ \ldots \ b_{Lout,Lout}]$ $xin = [\alpha_{1,-1} \ \alpha_{1,0} \ \alpha_{1,+1} \ \ldots \ \alpha_{Lin,Lin}]^t$ $xout = [\beta_{1,-1} \ \beta_{1,0} \ \beta_{1,+1} \ \ldots \ \beta_{Lout,Lout}]^t$

[Expression 11]

Then, the sensor output vector Φ can be expressed in a form of an inner product of the matrix S and the column vector X as in the expression below. In the expression, the matrix S represents the basis vectors which are acquired by the signal space separating section 860 from the basis vector storage section 850 in step 930 for example. A column vector X represents coefficients related to the basis vectors.

$$\Phi = SX = [Sin \ Sout] \begin{bmatrix} Xin \\ Xout \end{bmatrix}$$

[Expression 12]

The signal space separating section 860 according to the present embodiment determines the column vector X satisfying Φ=SX with least squares approximation using the expression below, based on a model formula of the sensor output vector Φ obtained with this Expression 12, in step 940. Thus, the signal space separating section 860 can solve the spatial distribution of the magnetic field in step 940. In other words, the spatial distribution of the magnetic field can be estimated. Specifically, the to-be-measured magnetic field can be estimated with φin_h=SinXin and the disturbance magnetic field can be estimated with φout_h=SoutXout. In this case, the signal space separating section 860 may issue an alert indicating that the to-be-measured magnetic field cannot be measured with high accuracy, when the magnitude of the disturbance magnetic field exceeds a predetermined range. With this configuration, the magnetic field measuring apparatus 10 can be prevented from measuring the to-be-measured magnetic field in advance, in such a situation as a case where the apparatus is under failure or a case where a large disturbance magnetic field disables the to-be-measured magnetic field to be measured with high accuracy. In such situations, for example, the signal space separating section 860 may determine that the magnitude of the disturbance magnetic field exceeds the predetermined range when the magnitude of any of the components of SoutXout exceeds a predetermined threshold, or when the sum or the average of the magnitude of each component of SoutXout exceeds a predetermined threshold.

$$X = \begin{bmatrix} Xin \\ Xout \end{bmatrix} = (S^t S)^{-1} S^t \Phi \qquad \text{[Expression 13]}$$

In step 950, the signal space separating section 860 reduces SoutXout using the column vector determined in step 940, and outputs a result of reducing the disturbance magnetic field components, that is, the components in the second term in Expression 8. By only outputting SinXin as a result, the signal space separating section 860 may output only the to-be-measured magnetic field component, that is, only the component in the first term in Expression 8, with the disturbance magnetic field components suppressed.

Thus, with the magnetic field measuring apparatus 10 according to the present embodiment, the signal separation can be performed to separate, into the to-be-measured magnetic field and the disturbance magnetic field, the spatial distribution of the magnetic field indicated by the magnetic field measurement data B measured by using the magnetic sensor array 210 configured by three-dimensionally arranging the magnetic sensor cells 220 with the plurality of sensor sections 300 capable of detecting the magnetic field in three axial directions. The magnetic field measuring apparatus 10 only outputs the to-be-measured magnetic field component with the disturbance magnetic field component suppressed, whereby the to-be-measured magnetic field can be measured with higher accuracy. Furthermore, since the sensor sections 300 each include magnetic flux concentrators, it is possible to increase the magnetic sensitivity of the sensor sections 300, clarify spatial sampling points, and increase the affinity with signal space separation technology. Furthermore, with the magnetic field measuring apparatus 10 including the calibration calculating section 830, highly accurate calibration can be implemented (such as main axis sensitivity mismatch, cross-axis sensitivities, and offset). Thus, a calibration error of the plurality of sensor sections 300 needs not to be processed in the signal space separation stage, because it can be reduced in an earlier stage, whereby the to-be-measured magnetic field component can be extracted with higher accuracy.

Figure 10:
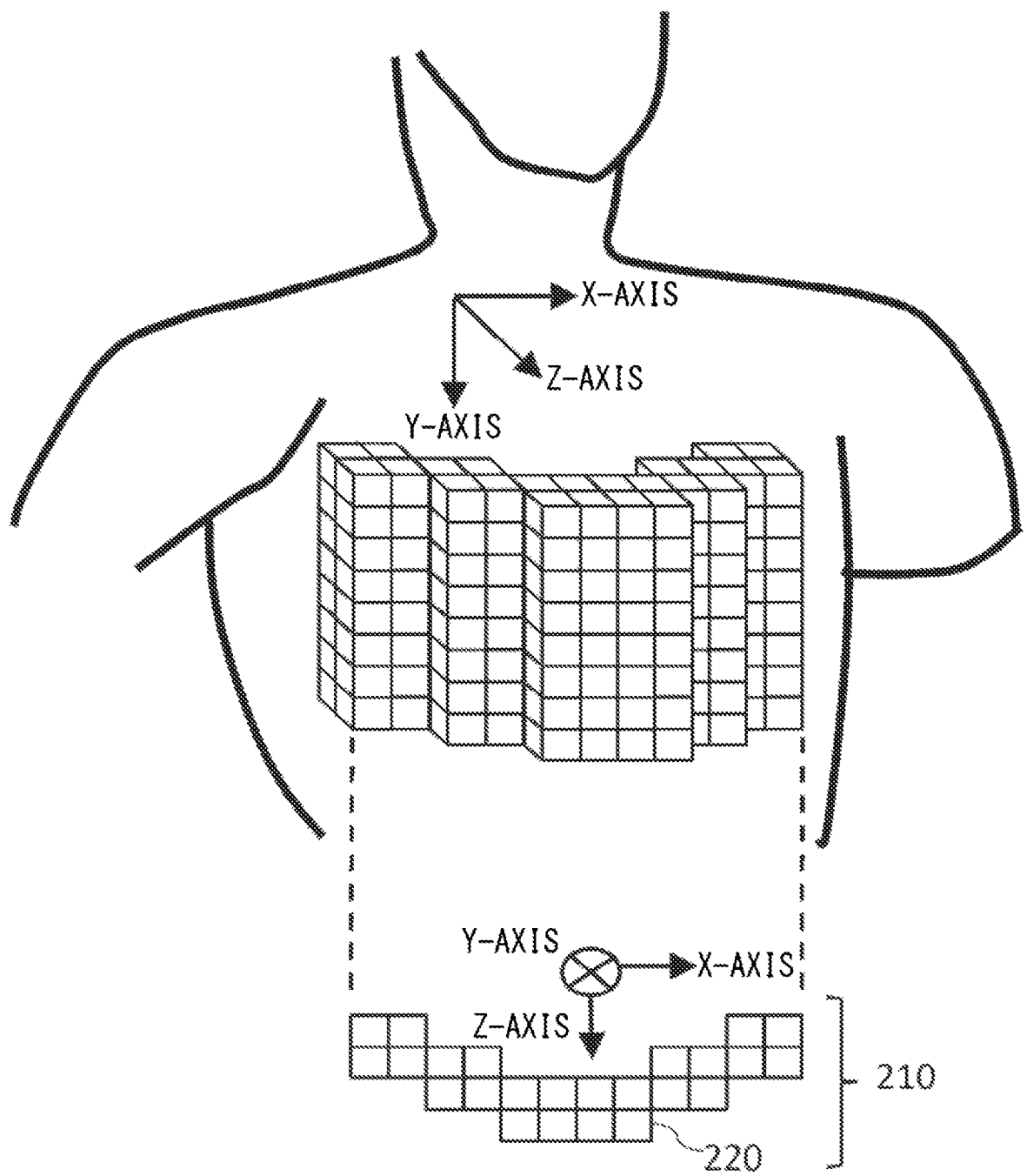
FIG. 10 illustrates an example where a magnetic field measuring apparatus 10 according to a modification of the present embodiment measures a cardiac magnetic field using a magnetic sensor array 210 arranged in a curved surface shape.

FIG. 10 illustrates an example where a magnetic field measuring apparatus 10 according to a modification of the present embodiment measures a cardiac magnetic field using a magnetic sensor array 210 arranged in a curved surface shape. In the present modification, the magnetic sensor array 210 has a plurality of magnetic sensor cells 220 arranged in each of the X direction, the Y direction, and the Z direction to have a curved surface shape (for example, a total of 192 magnetic sensor cells 220 with 12 cells arranged in the X direction, 8 cells arranged in the Y direction, and 2 cells arranged in the Z direction). The magnetic sensor cells 220 are arranged at respective grid points included in the curved surface shape in a three-dimensional lattice space. These grid points are points provided at predetermined regular intervals provided along the X direction, the Y direction, and the Z direction to form a lattice form. As one example, each magnetic sensor cell 220 is arranged along a curved surface protruding in a direction orthogonal to one of the X direction, the Y direction, and the Z direction, as viewed in one direction. The present drawing illustrates an example where each magnetic sensor cell 220 is arranged along a curved surface protruding in a positive direction of the Z-axis as viewed in the Y direction. In this case, for example, the magnetic sensor array 210 may form a curved surface shape protruding in the positive direction of the Z-axis, with the respective magnetic sensor cells 220 arranged at the respective grid points in the three-dimensional lattice space while having the respective vertices of the respective magnetic sensor cells 220 arranged in the negative direction of the Z-axis as much as possible without exceeding a predetermined curved surface protruding in the positive direction of the Z-axis.

As one example, the magnetic sensor array 210 according to the present embodiment has the magnetic sensor cells 220 formed to have a rectangular parallelepiped shape, so that the shape of the magnetic sensor array 210 can be easily changed. Thus, the magnetic sensor array 210 according to the present embodiment can have various shapes that can be formed with the magnetic sensor cells 220 arranged at grid points, and thus feature a high degree of freedom in design. Thus, the magnetic sensor array 210 can easily form a curved surface shape in a three dimensional space, with the plurality of magnetic sensor cells 220 arranged at the grid points included in the curved surface shape in the three dimensional space as illustrated in the present drawing.

In the present modification, the magnetic field measuring apparatus 10 measures the magnetic field, with the magnetic sensor array 210 arranged so that the chest of the subject is positioned on the center side of the curved surface, that is, the heart that is the to-be-measured magnetic field source is positioned on the center side of the curved surface. Thus, the magnetic field measuring apparatus 10 performs signal space separation using the magnetic field measurement data B measured at a position close to the heart that is the to-be-measured magnetic field source, and thus can highly accurately perform the separation into the to-be-measured magnetic field and the disturbance magnetic field. In this case, the magnetic sensor array 210 preferably has the curvature of the curved surface substantially the same as the curvature around the chest of the subject, so that the magnetic field can be measured at a position closer to the heart that is the to-be-measured magnetic field source.

Figure 11:
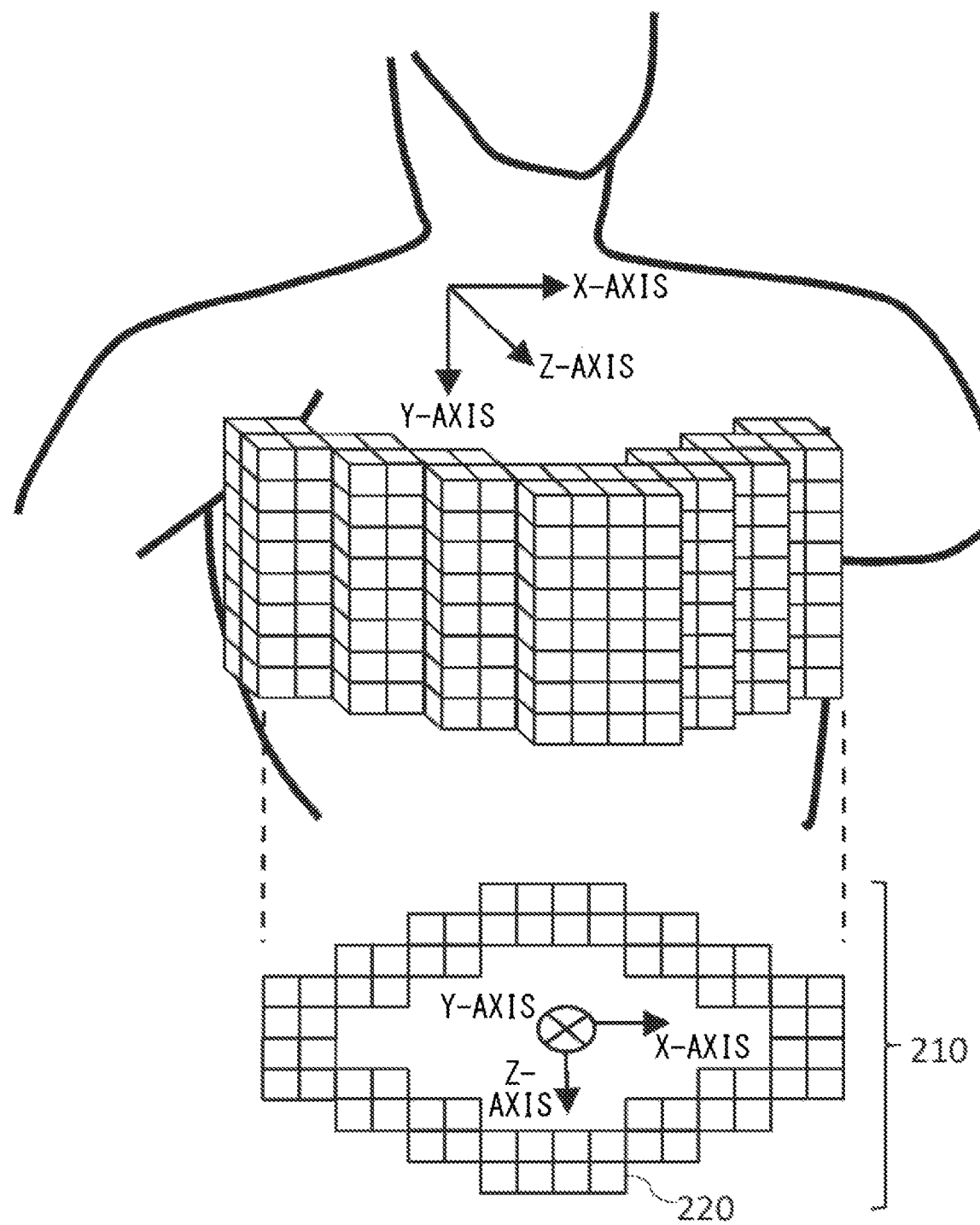
FIG. 11 illustrates an example where a magnetic field measuring apparatus 10 according to a modification of the present embodiment measures a cardiac magnetic field using a magnetic sensor array 210 arranged in a closed curved surface shape.

FIG. 11 illustrates an example where a magnetic field measuring apparatus 10 according to a modification of the present embodiment measures a cardiac magnetic field using a magnetic sensor array 210 arranged in a closed curved surface shape. In the present modification, the magnetic sensor array 210 has a plurality of magnetic sensor cells 220 arranged in each of the X direction, the Y direction, and the Z direction in a closed curved surface shape (for example, a total of 512 magnetic sensor cells 220 with 16 cells arranged in the X direction, 8 cells arranged in the Y direction, and 4 cells arranged in the Z direction). The magnetic sensor cells 220 are arranged at respective grid points included in the closed curved surface shape in a three-dimensional lattice space. Also in the present modification, the magnetic sensor array 210 includes the plurality of magnetic sensor cells 220 arranged along a curved surface protruding in a direction orthogonal to one direction of the X direction, the Y direction, and the Z direction, as viewed in one direction, as in FIG. 10. In the present modification, the magnetic sensor array 210 further includes a plurality of magnetic sensor cells 220 arranged along a curved surface that is recessed in a direction orthogonal to the one direction. The magnetic sensor array 210 forms the closed curved surface shape with the protruding curved surface shape and the recessed curved surface shape combined. As one example, the present drawing illustrates an example where the magnetic sensor array 210 includes a plurality of magnetic sensor cells 220 arranged along a curved surface protruding in the positive direction of the Z-axis as viewed in the Y direction and a plurality of magnetic sensor cells 220 arranged along a curved surface recessed in the positive direction of the Z-axis as viewed in the Y-direction, and forms the closed curved surface shape as a combination of the curved surface shapes respectively protruding and recessed in the positive direction in the Z-axis.

In the present modification, the magnetic field measuring apparatus 10 measures the magnetic field, with the magnetic sensor array 210 arranged so that the chest of the subject is surrounded by the closed curved surface, that is, the heart that is the to-be-measured magnetic field source is surrounded by the closed curved surface. With this configuration, the magnetic field measuring apparatus 10 measures a magnetic field generated on a front side of the subject due to electrical activity of the heart, as well as a magnetic field generated on a back side of the subject due to electrical activity of the heart, to perform signal space separation using the magnetic field measurement data B measured on the front side and the back side, and thus can more accurately perform separation into a to-be-measured magnetic field and a disturbance magnetic field. Also in the present modification, the magnetic sensor array 210 preferably has the curvature of the curved surface substantially the same as the curvature around the chest of the subject, so that the magnetic field can be measured at a position closer to the heart that is the to-be-measured magnetic field source, as in FIG. 10.

Now, results of simulating disturbance attenuation ratios, indicating disturbance magnetic field attenuation performance of the magnetic field measuring apparatus 10, obtained by different shapes of the magnetic sensor arrays 210 will be described.

FIGS. 12A to 12D illustrate magnetic sensor arrays 210 of different shapes used for simulating the disturbance attenuation ratio. FIG. 12A illustrates a magnetic sensor array 210 of a plate type illustrated in FIG. 2 having a first shape (a) having eight units in the vertical direction (X-axis direction)×eight units in the horizontal direction (Y-axis direction)×one unit in the height direction (Z-axis direction), where one unit is one three-axis magnetic sensor cell 220.

FIG. 12B illustrates a magnetic sensor array 210 of a curved type illustrated in FIG. 10 having a second shape (b) and having eight units in the vertical direction (X-axis direction)×eight units in the horizontal direction (Y-axis direction)×one unit in the height direction (Z-axis direction), and is curved in at least one direction. In the present drawing, the plurality of magnetic sensor cells 220 are arranged in such a manner that a Z-axis coordinate increases in the positive direction, toward the center of the X-axis direction of the magnetic sensor array 210, as viewed on a XZ plane. Thus, the magnetic sensor array 210 has a shape protruding in the positive direction of the Z-axis. Specifically, the magnetic sensor array 210 has a curved surface shape that is curved in at least one direction, with the curved surface shape formed as a substantially parabolic. Although the present drawing illustrates one example where the Z-axis coordinates of all the plurality of magnetic sensor cells 220 are the same along the Y-axis direction, the Z-axis coordinates of at least some of the plurality of magnetic sensor cells 220 along the Y-axis direction may be different. Although the present drawing illustrates one example where the plurality of magnetic sensor cells 220 are symmetrically arranged about the center in the X-axis direction of the magnetic sensor array 210, as viewed on the XZ plane, this should not be construed in a limiting sense. A plurality of magnetic sensor cells 220 paired in the X-axis direction, for example, at least some of the Z-axis coordinates of a plurality of magnetic sensor cells 220 arranged at both ends in the X-axis direction, may be different. Although (b) in the present drawing illustrates one example where the Y-axis coordinates of all the plurality of magnetic sensor cells 220 are the same along the X-axis direction as viewed on an XY plane, the Y-axis coordinates of at least some of the plurality of magnetic sensor cells 220 along the X-axis direction may be different.

FIG. 12C illustrates a magnetic sensor array 210 of a cylindrical type illustrated in FIG. 11 having a third shape (c) and having eight sensor groups arranged to form an elliptical shape on the XZ plane, with each sensor cell group having magnetic sensor cells 220 arranged to be eight in the horizontal direction (y-axis direction)×one in the height direction (z-axis direction) defined as one group, and with two arrays curved in at least one direction(magnetic sensor arrays each including four sensor group in a curved form in this case) and symmetrically arranged in an annular form.

FIG. 12D illustrates a magnetic sensor array 210 having a fourth shape (2b) including two stages of magnetic sensor arrays 210 in (b) overlapped in the Z-axis direction, that is, including an array of eight cell in the horizontal direction (X-axis direction)×eight cell in the horizontal direction (Y-axis direction)×two cells in the height direction (Z-axis direction) and curved in at least one direction. The stage is used for counting and referring to each layer in a layout with the magnetic sensor cells 220 arranged in a layered structure in one direction away from the curved surface covering the signal source space.

The interval between the magnetic sensor cells 220 is 40 mm. The simulation was performed with Lin set to be 6 and Lout set to be 4. In the plate type illustrated in (a), the calculation origin was a position separated from the center of the surface of the magnetic sensor array 210 by 4 cm in the −Z direction. In the curved types in (b) and (2b), the origin was a position separated from the center (center as viewed on the XY plane) point of the surface of the magnetic sensor array 210 by 4 cm in the −Z direction. In the cylindrical type in (c), the origin was the XY plane coordinates of the center of the magnetic sensor array 210 in the XY direction, and the XZ plane coordinates of the center of a circle approximating the outer shape of the magnetic sensor array 210 as viewed in the Y direction.

The following table illustrates results of simulating (1) a disturbance attenuation ratio in a case where a disturbance noise source is placed at a position separated by 3 m, and (2) a reduction rate of sensor noise, for each of the (a) plate type, (b) curved type, and (c) cylindrical type shapes.

TABLE 1

| SHAPE | (a) PLATE | (b) CURVED | (c) CYLINDRICAL |
| --- | --- | --- | --- |
| (1) DISTURBANCE ATTENUATION RATIO (dB) | −79.75 | −85.70 | −87.11 |
| (2) SENSOR NOISE REDUCTION RATIO (dB) | −0.80 | −5.09 | −5.31 |

The following table illustrates comparison in performance of the curved type between (b) a single stage structure with one magnetic sensor cell 220 provided in the Z-axis direction, and (2b) two stage structure with two magnetic sensor cells 220 provided in the Z-axis direction.

TABLE 2

| SHAPE | (b) SINGLE STAGE | (2b) TWO STAGES |
| --- | --- | --- |
| (1) DISTURBANCE ATTENUATION RATIO (dB) | −85.70 | −91.34 |
| (2) SENSOR NOISE REDUCTION RATIO (dB) | −5.09 | −8.89 |

Thus, from the above, it can be seen that the modifications illustrated in FIG. 10 and FIG. 11 has a superior disturbance magnetic field attenuation performance to that in the example of the present embodiment illustrated in FIG. 2. Thus, the magnetic sensor cells are preferably arranged along a curved surface as illustrated in FIG. 10 and FIG. 11, for observing the cardiac magnetic field without being affected by the disturbance magnetic field. This is because the magnetic field expressed by Expression 8 can be easily approximated with a curved shape compared with a plate type. For the same reason, noise of a sensor is easily identified as disturbance and reduced. Furthermore, it can be seen that regarding the curved type in FIG. 10, the two stage structure with two magnetic sensor cells arranged in the Z-axis direction has superior disturbance attenuation ratio to that of the single stage structure with one magnetic sensor cell arranged in the Z-axis direction. This is because a detailed change in the magnetic field can be more easily identified with the two stage structure. The two stage structure is also preferable because a change in the magnetic field in the Z-axis direction can be monitored, and thus the cardiac magnetic field can be three-dimensionally observed. The number of layers can further be increased, and thus a configuration with more than two stages may be used.

Figure 13:
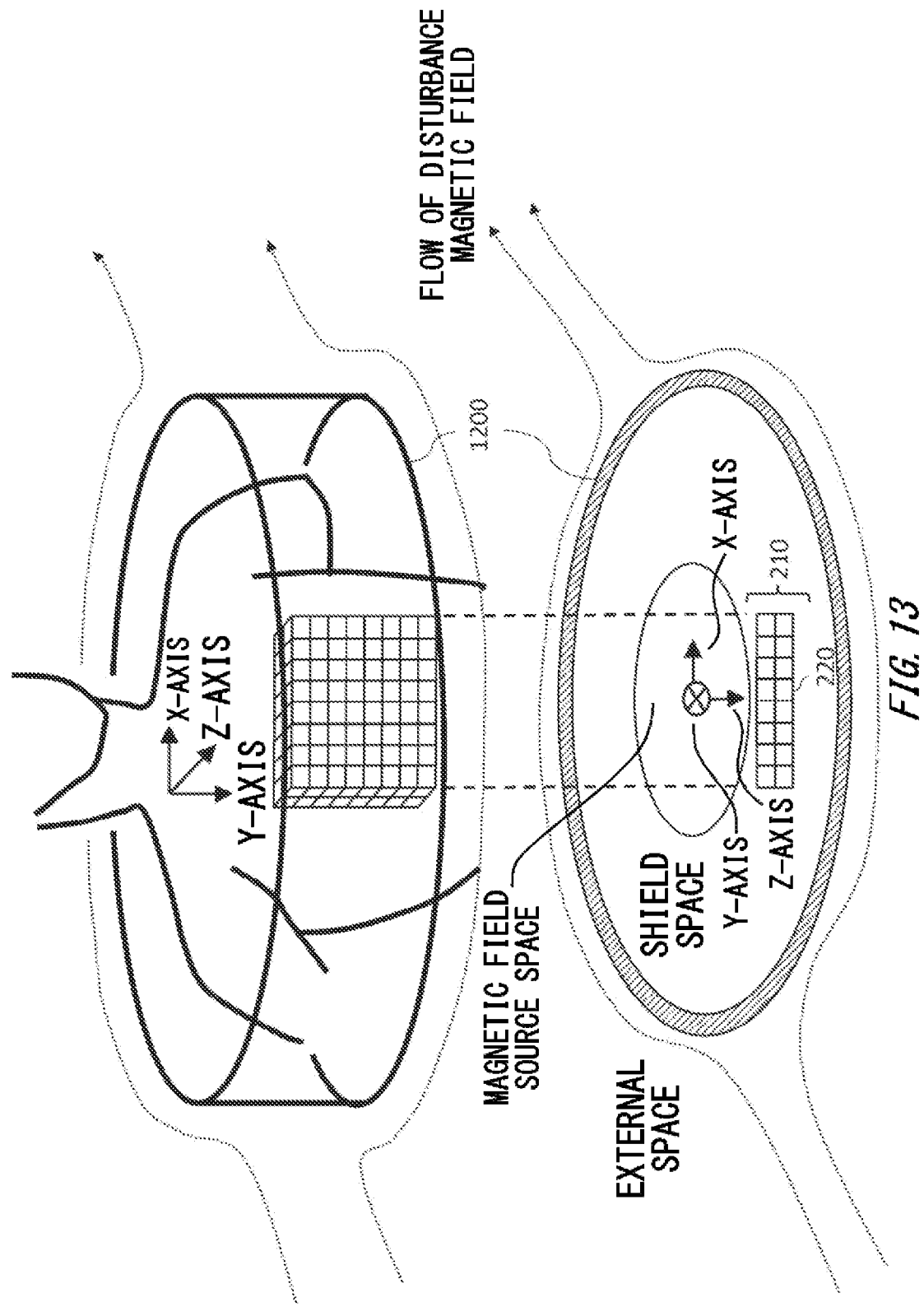
FIG. 13 illustrates an example where a magnetic field measuring apparatus 10 according to a modification of the present embodiment measures a cardiac magnetic field using a magnetic shield 1200.

FIG. 13 illustrates an example where a magnetic field measuring apparatus 10 according to a modification of the present embodiment measures a cardiac magnetic field using a magnetic shield 1200. In the present modification, the magnetic field measuring apparatus 10 uses the magnetic shield 1200 for measuring a cardiac magnetic field.

The magnetic shield 1200 is formed by a high permeability material such as permalloy (Ni—Fe alloy) and mu-metal (alloy obtained by adding Cu and Cr to permalloy) for example. As one example, the magnetic shield 1200 has a hollow cylindrical shape, and is arranged to surround the chest of the subject and the magnetic sensor array 210, so that the chest of the subject and the magnetic sensor array 210 are positioned in the hollow space. Here, the chest of the subject including the to-be-measured magnetic field source (heart) is defined as a magnetic field source space, a space that is on the outer side of the magnetic field source space and is surrounded by an inner wall of the magnetic shield 1200 is defined as a shield space, and a space more on the outer side than an outer wall of the magnetic shield 1200 is defined as an external space. In this case, the magnetic sensor array 210 is positioned within the shield space.

The magnetic shield 1200 is formed by the high permeability material as described above and thus well absorbs magnetic flux. Thus, a disturbance magnetic field (including the earth magnetism and the like) from the external space can be distributed along the surface of the magnetic shield 1200. Thus, the magnetic shield 1200 can largely reduce the disturbance magnetic field (including the earth magnetism and the like) entering the shield space, and can prevent the spatial distribution of the magnetic field inside the shield space from being complicated.

Thus, with the present modification, the magnetic field measuring apparatus 10 performs the signal space separation with the disturbance magnetic field reduced and simplified, whereby the to-be-measured magnetic field and the disturbance magnetic field can be more accurately separated.

In the modification illustrated in FIG. 13, an example is described where the magnetic shield 1200 is used in a case where the magnetic field measuring apparatus 10 measures the cardiac magnetic field using the magnetic sensor array 210 arranged in a planar shape. Still, the magnetic field measuring apparatus 10 can similarly use the magnetic shield 1200 in a case where the cardiac magnetic field is measured using the magnetic sensor array 210 arranged in a curved surface shape as illustrated in FIG. 10 and in a closed curved surface shape as illustrated in FIG. 11.

Figure 14:
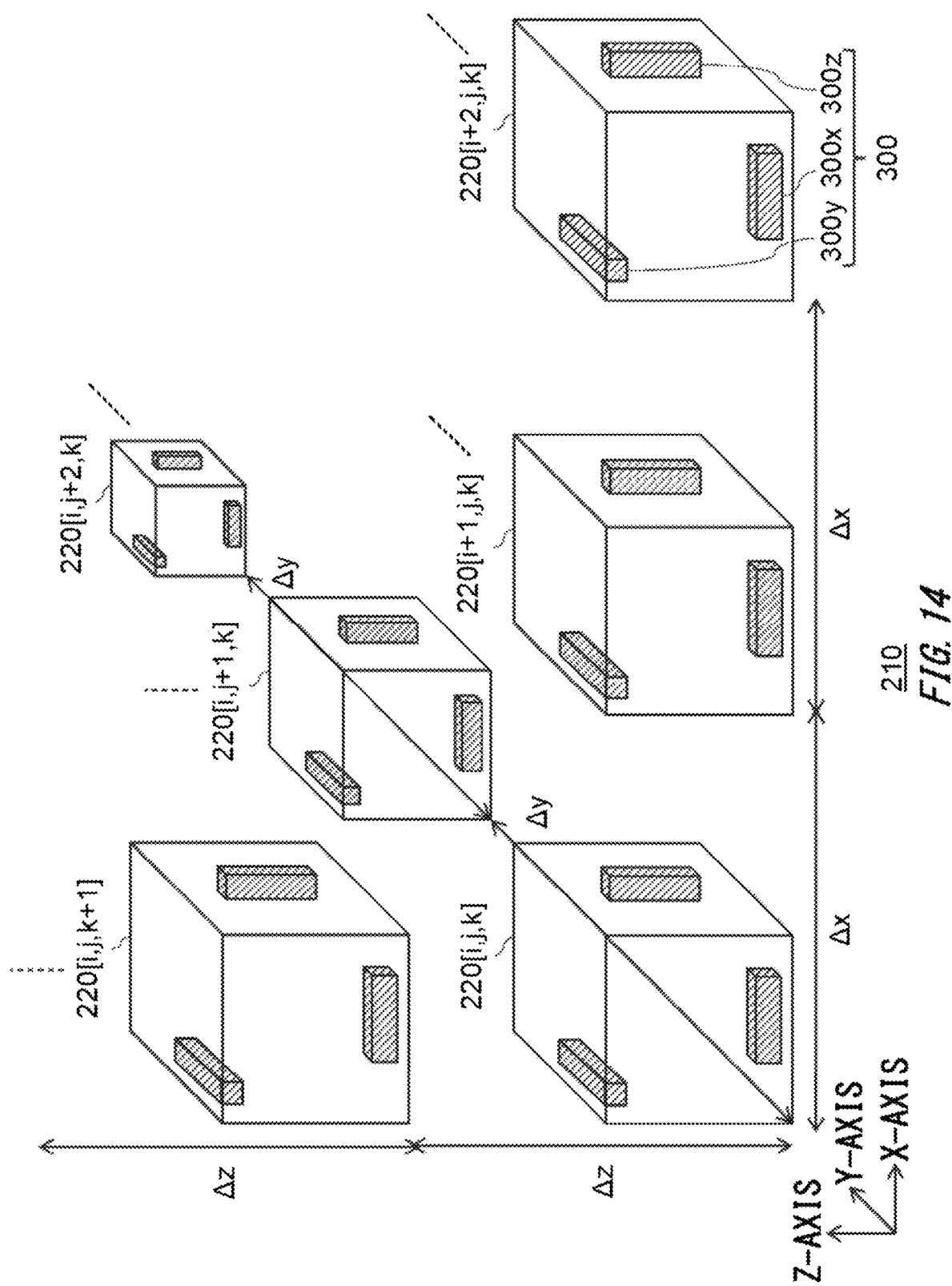
FIG. 14 illustrates a modification of the magnetic sensor array 210 according to the present embodiment.

FIG. 14 illustrates a modification of the magnetic sensor array 210 according to the present embodiment. In FIG. 14, components having the same function and configuration as in FIG. 3 are given the same reference numerals, and the following describes only differing points. In the present drawing, each of the plurality of magnetic sensor cells 220 of the magnetic sensor array 210 is provided with the sensor sections 300x, 300y, and 300z with no air space (gap) provided at a corner portion. Even when the sensor sections 300 are thus arranged, the plurality of magnetic sensor cells 220 can each be arranged without the sensor sections 300x, 300y, and 300z overlapping as viewed in any of the three-dimensional direction on the X-axis, the Y-axis, and the Z-axis. With this arrangement, the plurality of sensor sections 300x, 300y, and 300z can be arranged in a dispersed manner in the magnetic sensor cell 220, whereby the plurality of sensor sections 300x, 300y, and 300z can be prevented from being arranged at a single corner portion in a concentrated manner. The magnetic field measuring apparatus 10 according to the present embodiment may acquire the measurement data using the magnetic sensor array 210 having the sensor sections 300 thus arranged.

A variety of embodiments of the present invention may be described with reference to flowcharts and block diagrams, where the blocks may represent: (1) steps of processes in which operations are performed; or (2) sections of devices responsible for performing the operations. Certain steps and sections may be implemented by dedicated circuitry, programmable circuitry supplied together with computer readable instructions stored on the computer readable medium, and/or a processor supplied together with computer readable instructions stored on the computer readable medium. Dedicated circuitry may include digital and/or analog hardware circuits and may include integrated circuits (IC) and/or discrete circuits. Programmable circuitry may include reconfigurable hardware circuits comprising, for example, logical AND, logical OR, logical XOR, logical NAND, logical NOR, and other logical operations, and memory elements such as flip-flops, registers, field-programmable gate arrays (FPGA), programmable logic arrays (PLA) or other.

Computer readable medium may include any tangible device that can store instructions for execution by a suitable device, such that the computer readable medium having instructions stored thereon comprises a product including instructions which can be executed to create means for performing operations specified in the flowcharts or block diagrams. Examples of computer readable medium may include an electronic storage medium, a magnetic storage medium, an optical storage medium, an electromagnetic storage medium, a semiconductor storage medium, or other. More specific examples of computer readable medium may include a floppy (registered trademark) disk, a diskette, a hard disk, a random access memory (RAM), a read-only memory (ROM), an erasable programmable read-only memory (EPROM or Flash memory), an electrically erasable programmable read-only memory (EEPROM), a static random access memory (SRAM), a compact disc read-only memory (CD-ROM), a digital versatile disk (DVD), a Blu-ray (registered trademark) disc, a memory stick, an integrated circuit card, or other.

Computer readable instructions may include assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk (registered trademark), JAVA (registered trademark), C++, etc., and conventional procedural programming languages, such as the "C" programming language or similar programming languages.

Computer readable instructions may be provided to a processor of a general-purpose computer, an application specific computer, or other programmable data processing device, or to programmable circuitry, locally or via a local area network (LAN), wide area network (WAN) such as the Internet or other, to execute the computer readable instructions to create means for performing operations specified in the flowcharts or block diagrams. Examples of processors include computer processors, processing units, microprocessors, digital signal processors, controllers, microcontrollers, or other.

Figure 15:
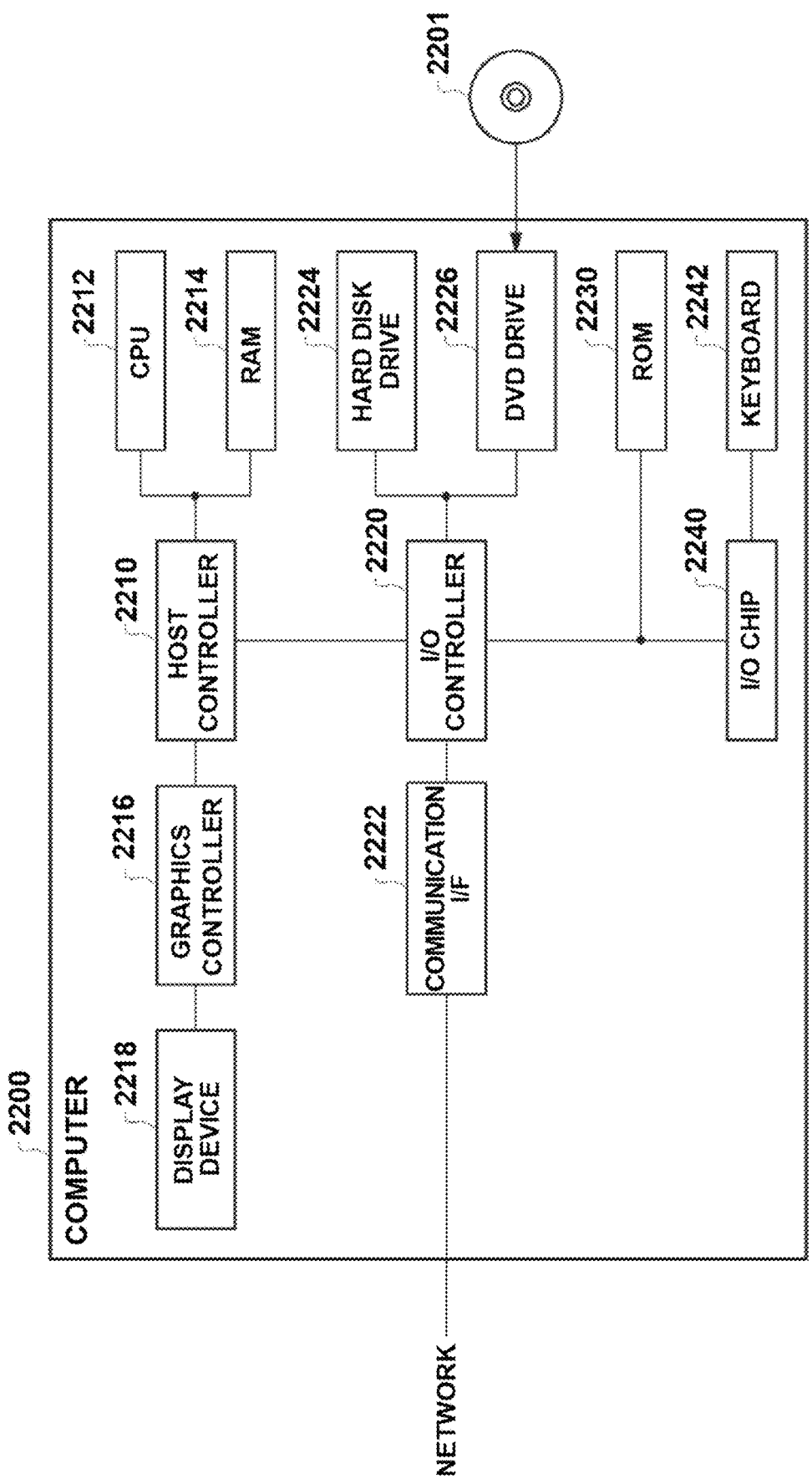
FIG. 15 illustrates an example of a computer 2200 through which a plurality of aspects of the present invention may be entirely or partially embodied.

FIG. 15 illustrates an example of a computer 2200 in which the plurality of aspects of the present invention may be wholly or partially embodied. A program that is installed in the computer 2200 can cause the computer 2200 to function as or perform operations associated with the device according to the embodiments of the present invention or one or more sections of said device, or perform said operations or said one or more sections, and/or cause the computer 2200 to perform the processes according to the embodiments of the present invention or steps of said processes. Such a program may be executed by the CPU 2212 to cause the computer 2200 to perform certain operations associated with some or all of the blocks of flowcharts and block diagrams described herein.

The computer 2200 according to the present embodiment includes a CPU 2212, an RAM 2214, a graphic controller 2216, and a display device 2218, which are mutually connected by a host controller 2210. The computer 2200 also includes input/output units such as a communication interface 2222, a hard disk drive 2224, a DVD-ROM drive 2226 and an IC card drive, which are connected to the host controller 2210 via an input/output controller 2220. The computer also includes legacy input/output units such as an ROM 2230 and a keyboard 2242, which are connected to the input/output controller 2220 via an input/output chip 2240.

The CPU 2212 operates according to programs stored in the ROM 2230 and the RAM 2214, thereby controlling each unit. The graphic controller 2216 obtains image data generated by the CPU 2212 on a frame buffer or other provided in the RAM 2214 or in itself, and causes the image data to be displayed on the display device 2218.

The communication interface 2222 communicates with other electronic devices via the network. The hard disk drive 2224 stores programs and data used by the CPU 2212 in the computer 2200. The DVD-ROM drive 2226 reads the programs or the data from the DVD-ROM 2201, and provides the hard disk drive 2224 with the programs or the data via the RAM 2214. The IC card drive reads programs and data from an IC card, and/or writes programs and data into the IC card.

The ROM 2230 stores therein a boot program or other to be executed by the computer 2200 when activated, and/or a program which depends on the hardware of the computer 2200. The input/output chip 2240 may also connect a variety of input/output units to the input/output controller 2220, via a parallel port, a serial port, a keyboard port, a mouse port, or other.

A program is provided by computer readable medium such as the DVD-ROM 2201 or an IC card. The program is read from the computer readable medium, installed into the hard disk drive 2224, RAM 2214, or ROM 2230, which are also examples of computer readable media, and executed by the CPU 2212. The information processing described in these programs is read into the computer 2200, which results in cooperation between a program and a variety of types of hardware resources mentioned above. The device or the method may be configured by realizing the operation or processing of information in accordance with the use of the computer 2200.

For example, when communication is executed between the computer 2200 and an external device, the CPU 2212 may execute a communication program loaded onto the RAM 2214 and instruct the communication interface 2222 to perform communication processing based on the processing described in the communication program. Under the control of the CPU 2212, the communication interface 2222 reads transmission data stored in a transmit buffer processing area provided in a recording medium such as the RAM 2214, the hard disk drive 2224, the DVD-ROM 2201, or the IC card, and then transmits the read transmission data to the network or writes reception data received from the network in a receive buffer processing area etc. provided in the recording medium.

In addition, the CPU 2212 may cause all or a necessary portion of a file or a database to be read into the RAM 2214, the file or the database having been stored in an external recording medium such as the hard disk drive 2224, the DVD-ROM drive 2226 (DVD-ROM 2201), the IC card or other, and perform a variety of types of processing on the data on the RAM 2214. The CPU 2212 may then write back the processed data to the external recording medium.

A variety of types of information, such as a variety of types of programs, data, tables, and databases, may be stored in the recording medium to undergo information processing. The CPU 2212 may perform a variety of types of processing on the data read from the RAM 2214, which includes a variety of types of operations, information processing, condition determination, conditional branch, unconditional branch, retrieval/replacement of information or other, as described anywhere throughout this disclosure and designated by an instruction sequence of programs, and writes the result back to the RAM 2214. In addition, the CPU 2212 may retrieve information in a file, a database or other, in a recording medium. For example, if a plurality of entries are stored in the recording medium, where each entry has an attribute value of a first attribute associated with an attribute value of a second attribute, the CPU 2212 may retrieve an entry which matches the condition having a designated attribute value of the first attribute, from among said plurality of entries, and read the attribute value of the second attribute stored in said entry, thereby obtaining the attribute value of the second attribute associated with the first attribute which meets the predetermined condition.

The program or software modules described above may be stored in the computer readable medium on the computer 2200 or in the vicinity of the computer 2200. In addition, a recording medium such as a hard disk or an RAM provided in a server system connected to a dedicated communication network or the Internet can be used as the computer readable medium, thereby providing the program to the computer 2200 via the network.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the present invention.

The operations, procedures, steps, and stages of each process performed by an apparatus, system, program, and method illustrated in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

10: magnetic field measuring apparatus, 100: main body, 110: magnetic sensor unit, 120: head, 125: driving section, 130: base portion, 140: pole portion, 150: information processing section, 210: magnetic sensor array, 220: magnetic sensor cell, 230: sensor data gathering section, 300: sensor section, 520: magnetic sensor, 530: magnetic field generating section, 532: amplifier circuit, 534: coil, 540: output section, 702: magnetoresistive element, 704, 706: magnetic flux concentrator, 800: sensor data processing section, 810: AD converter, 812: clock generator, 820: magnetic field acquiring section, 830: calibration calculating section, 840: data output section, 850: basis vector storage section, 860: signal space separating section, 1200: magnetic shield, 2200: computer, 2201: DVD-ROM, 2210: host controller, 2212: CPU, 2214: RAM, 2216: graphics controller, 2218: display device, 2220: input/output controller, 2222: communication interface, 2224: hard disk drive, 2226: DVD-ROM drive, 2230: ROM, 2240: input/output chip, 2242: keyboard

What is claimed is:

1. A magnetic field measuring apparatus comprising:
   a magnetic sensor array configured with a plurality of magnetic sensor cells being three-dimensionally arranged, wherein each of the plurality of magnetic sensor cells is capable of detecting a magnetic field in three axial directions, and each of the plurality of magnetic sensor cells includes a plurality of magnetic sensors each having a magnetoresistive element;
   at least one processor;
   a magnetic field acquiring section configured to acquire measurement data measured by the magnetic sensor array; and
   a signal space separating section configured to perform, using the at least one processor, signal separation on a spatial distribution of the magnetic field indicated by the measurement data, based on basis vectors calculated from orthonormal functions and a position and magnetic sensitivity of each magnetic sensor of the magnetic sensor array, wherein
   each of the magnetic sensor cells comprises:
   a magnetic field generating section configured to generate a feedback magnetic field to reduce an input magnetic field detected by each of the magnetic sensors; and
   an output section configured to output an output signal corresponding to a feedback current that is to flow in order for the magnetic field generating section to generate the feedback magnetic field.

2. The magnetic field measuring apparatus according to claim 1, wherein the signal space separating section performs, using the at least one processor, the signal separation to separate the spatial distribution of the magnetic field into a to-be-measured magnetic field and a disturbance magnetic field.

3. The magnetic field measuring apparatus according to claim 2, wherein the signal space separating section suppresses, using the at least one processor, the disturbance magnetic field to calculate the to-be-measured magnetic field.

4. The magnetic field measuring apparatus according to claim 1, wherein the signal space separating section performs, using the at least one processor, the signal separation on the spatial distribution of the magnetic field, through series expansion of the basis vectors.

5. The magnetic field measuring apparatus according to claim 2, wherein the signal space separating section performs, using the at least one processor, the signal separation on the spatial distribution of the magnetic field, through series expansion of the basis vectors.

6. The magnetic field measuring apparatus according to claim 3, wherein the signal space separating section performs, using the at least one processor, the signal separation on the spatial distribution of the magnetic field, through series expansion of the basis vectors.

7. The magnetic field measuring apparatus according to claim 4, wherein the signal space separating section calculates, using the at least one processor, expansion coefficients of the basis vectors using a least-squares method.

8. The magnetic field measuring apparatus according to claim 1, wherein the orthonormal functions are expressed with spherical harmonics.

9. The magnetic field measuring apparatus according to claim 2, wherein the orthonormal functions are expressed with spherical harmonics.

10. The magnetic field measuring apparatus according to claim 1, wherein the magnetic sensors each further include magnetic flux concentrators arranged on both one end and the other end of the magnetoresistive element.

11. The magnetic field measuring apparatus according to claim 2, wherein the magnetic sensors each further include magnetic flux concentrators arranged on both one end and the other end of the magnetoresistive element.

12. The magnetic field measuring apparatus according to claim 1, further comprising a calibration calculating section configured to calibrate, using the at least one processor, the measurement data acquired by the magnetic field acquiring section.

13. The magnetic field measuring apparatus according to claim 2, further comprising a calibration calculating section configured to calibrate, using the at least one processor, the measurement data acquired by the magnetic field acquiring section.

14. The magnetic field measuring apparatus according to claim 1, wherein the magnetic sensor array is formed in two stages.

15. The magnetic field measuring apparatus according to claim 2, wherein the magnetic sensor array is formed in two stages.

16. The magnetic field measuring apparatus according to claim 1, wherein in the magnetic sensor array, the magnetic sensor cells are three-dimensionally arranged to be positioned at grid points between two curved surfaces curved in one direction.

17. The magnetic field measuring apparatus according to claim 2, wherein in the magnetic sensor array, the magnetic sensor cells are three-dimensionally arranged to be positioned at grid points between two curved surfaces curved in one direction.

18. The magnetic field measuring apparatus according to claim 16, wherein the curved surfaces are formed to be substantially parabolic.

* * * * *